US008993773B2

(12) United States Patent
Pandey et al.

(10) Patent No.: US 8,993,773 B2
(45) Date of Patent: Mar. 31, 2015

(54) PROCESS TO PREPARE PIOGLITAZONE VIA SEVERAL NOVEL INTERMEDIATES

(71) Applicant: Cadila Healthcare Limited, Gujarat (IN)

(72) Inventors: Bipin Pandey, Gujarat (IN); Vidya Bhushan Lonray, Gujarat (IN); Braj Bhushan Lohray, Gujarat (IN)

(73) Assignee: Cadila Healthcare Limited, Gujarat (IN)

( * ) Notice: Subject to any disclaimer, the term of this patent is extended or adjusted under 35 U.S.C. 154(b) by 21 days.

(21) Appl. No.: 13/625,110

(22) Filed: Sep. 24, 2012

(65) Prior Publication Data

US 2014/0088127 A1   Mar. 27, 2014

Related U.S. Application Data

(62) Division of application No. 13/305,295, filed on Nov. 28, 2011, now Pat. No. 8,445,685, which is a division of application No. 12/896,844, filed on Oct. 2, 2010, now Pat. No. 8,173,816, which is a division of application No. 12/010,473, filed on Jan. 25, 2008, now Pat. No. 7,863,300, which is a division of application No. 10/520,166, filed as application No. PCT/IN03/00241 on Jul. 15, 2003, now Pat. No. 7,465,801.

(30) Foreign Application Priority Data

Jul. 16, 2002  (IN) .......................... 648/MUM/2002

(51) Int. Cl.
 *C07D 213/48* (2006.01)
(52) U.S. Cl.
 USPC ....................................... 546/340
(58) Field of Classification Search
 CPC .............................. C07D 213/48; A61K 31/44
 USPC .......................... 546/340; 514/277
 See application file for complete search history.

(56) References Cited

U.S. PATENT DOCUMENTS

| 4,287,200 A | 9/1981 | Kawamatsu et al. |
| 4,340,605 A | 7/1982 | Kawamatsu et al. |
| 4,438,141 A | 3/1984 | Kawamatsu et al. |
| 4,444,779 A | 4/1984 | Kawamatsu et al. |
| 4,687,777 A | 8/1987 | Meguro et al. |
| 4,812,570 A | 3/1989 | Meguro et al. |
| 4,898,947 A | 2/1990 | Meguro et al. |
| RE36,575 E | 2/2000 | Meguro et al. |
| 7,465,801 B2 | 12/2008 | Pandey et al. |
| 7,671,207 B2 | 3/2010 | Pandey et al. |
| 7,863,300 B2 | 1/2011 | Pandey et al. |
| 8,173,816 B2 | 5/2012 | Pandey et al. |
| 2006/0167061 A1 | 7/2006 | Pandey et al. |
| 2008/0004446 A1 | 1/2008 | Pandey et al. |
| 2008/0300282 A1 | 12/2008 | Pandey et al. |
| 2011/0021576 A1 | 1/2011 | Pandey et al. |
| 2012/0077848 A1 | 3/2012 | Pandey et al. |

FOREIGN PATENT DOCUMENTS

| EP | 0008203 | 2/1980 |
| EP | 0193256 | 9/1986 |
| EP | 0257781 | 3/1988 |
| WO | 93/22445 | 11/1993 |
| WO | 02/88120 | 11/2002 |

OTHER PUBLICATIONS

Carpenter et al., "Process Development and Scale, etc.," Organic Process Research & Development 2002, 6, 721-728.*
Momose et al. "Studies on antidiabetic agents. X. Synthesis and biological activities of pioglitazone and related compounds" Chem. Pharm. Bull. 39:1440-1445 (1991).
Sohda et al. "Studies on antidiabetic agents. Synthesis and hypoglycemic activity of 5-[4-(pyridylalkoxy)-benzyl]-2,4-thiazolidinediones" Arzneim.-Forsch. Drug Research 40:37-42 (1990).
Int'l Search Report for PCT/IN2003/00241, four pages, mailed Feb. 5, 2004.
Written Opinion for PCT/IN2003/00241, two pages, mailed Apr. 6, 2004.
Int'l Preliminary Examination Report for PCT/IN2003/00241, five pages, completed Oct. 20, 2004.

* cited by examiner

*Primary Examiner* — Patricia L Morris
(74) *Attorney, Agent, or Firm* — Nixon & Vanderhye P.C.

(57) ABSTRACT

A novel process for preparing thiazolidinediones, preferably Pioglitazone, as described. Also described are novel intermediates involved in its synthesis and process for their preparation and use in medicine.

4 Claims, No Drawings

PROCESS TO PREPARE PIOGLITAZONE VIA SEVERAL NOVEL INTERMEDIATES

This is a divisional of application Ser. No. 13/305,295, filed Nov. 28, 2011, now U.S. Pat. No. 8,445,685; which is a divisional of application Ser. No. 12/896,844, filed Oct. 2, 2010, now U.S. Pat. No. 8,173,816; which is a divisional of application Ser. No. 12/010,473, filed Jan. 25, 2008, now U.S. Pat. No. 7,863,300; which is a divisional of application Ser. No. 10/520,166, filed Oct. 4, 2005, now U.S. Pat. No. 7,465,801; which is the U.S. national stage under 35 USC 371 of Int'l Application No. PCT/IN2003/000241, filed Jul. 15, 2003 which designated the U.S. and claims the benefit of priority from Indian Application No. 648/MUM/2002, filed Jul. 16, 2002; the entire contents of which are hereby incorporated by reference in this application.

FIELD OF INVENTION

The present invention relates to a novel process for the production of various pyridine substituted 5-[4-[2-(alkyl substituted pyridyl)ethoxy]benzyl-2,4-thiazolidinedione derivatives of general formula 1, and their pharmaceutically acceptable salts. The present invention also discloses novel compounds which are suitable as intermediates for the preparation of such thiazolidinediones.

Compounds of formula 1 are known to exhibit hypoglycemic and hypolipidemic activities. The present invention also relates to the novel intermediates of formula 3, 5, 6, 9, 10(b), 11, 13, 14 (Scheme I, II, III) and their corresponding salts, used either as a racemate or in optically pure form to prepare compounds of general formula 1. Such novel compounds of the present invention can also be suitably formulated for treatment of diabetes, hyperlipidemia and obesity or diseases caused by insulin resistance as a pathophysiological mechanism. This invention, in particular, relates to a novel process for the production of 5-[4-[2-(5-ethylpyridyl)ethoxy]benzyl-2,4-thiazolidinedione (Pioglitazone hydrochloride, R in 1 is 5-ethyl).

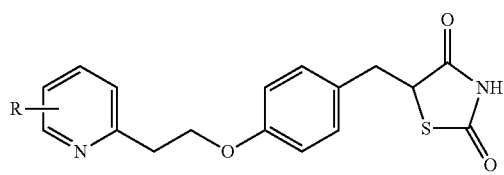

1

BACKGROUND OF THE INVENTION

The present invention provides a process to prepare various pyridine substituted 5-[4-[2-(alkyl substituted pyridyl)ethoxy]benzyl-2,4-thiazolidinedione derivatives of general formula 1, and their pharmaceutically acceptable salts. These compounds have been found to be advantageous for their therapeutic applications eg. antidiabetic and hypolipidemic, especially as insulin sensitizing agents. Such compounds have been described in U.S. Pat. No. 4,687,777 and EP 193256. EP 0508740 discloses Pyridine N-oxide analogues of thiazolidinedione derivatives, including the N-oxide of Pioglitazone (1), having antidiabetic and hypolipidemic activity. U.S. Pat. No. 4,444,779 and EP 008203 discloses new thiazolidinedione compounds, including ciglitazone and their pharmaceutically acceptable salts thereof, which have similar antidiabetic properties.

Diabetes affects a large population and this condition is associated with a number of other complications. Usually, the disease is associated with other disease conditions such as obesity, hyperlipidemia, hypertension and angina. It is a well-recognized fact that improper treatment can aggravate impaired glucose tolerance and insulin resistance, leading to frank diabetes. Thiazolidinediones of formula 1 as well as the novel intermediates 14 & 13 of the present invention are useful in the treatment of diabetes, and affect lipid metabolism.

Pioglitazone belongs to the thiazolidinedione group of antidiabetics. Later it has been found that its antidiabetic effect consists in reducing insulin resistance, thereby improving glucose homeostases without increasing insulin secretion, unlike most other antidiabetics. For these extraordinary characteristics this product is of great importance for the treatment of non-insulin dependent diabetes mellitus. Combination with insulin or other antidiabetics can further increase its effect.

Methods for production of various thiazolidinedione derivatives are described in U.S. Pat. No. 4,687,777; *Drugs of Future*, 15, 1080(1990); *Chemical and Pharmaceutical Bulletin*, 30, 3563(1982); 30, 3580(1982) and 32, 2267(1984). These methods invariably comprise low temperature diazotisation, condensation with lachrymetric and readily polymerizable reagent acrylic ester in the presence of a copper catalyst by Meerwein arylation reaction to give a haloester, reacting it with thiourea to give an iminothiazolidine and finally hydrolyzing the same to get the required thiazolidinedione derivative. These methods include multistep synthetic processes and sometimes it is difficult to control Meerwein reaction at industrial scale, since it is an exothermic run-away type of reaction accompanied by the generation of a large amount of nitrogen gas, which is difficult to handle. Moreover, due to byproduct formation, purification becomes cumbersome. Besides, special measures are required in the Meerwein reaction for elimination of an extremely bad odour of acrylic acid ester, which must be used in excess. The disposal of excess material, along with heavy metals, requires additional effluent treatment protocols. These issues make the known route disadvantageous both technically and commercially.

Subsequently, new synthetic strategies have been reported in EP 0257781, which might lead to side product(s) eg. 2-vinyl-5-ethyl pyridine from tosylates, and require high pressure Raney Ni conversion of cyanide to formyl group. The purification of the intermediates is also difficult in this process. In an yet another invention, microbial reductase has been employed to obtain pharmaceutically active thiazolidine derivatives (WO 9310254).

Recently, Pioglitazone oxygenated metabolites have been patented (WO 9322445) as potentially useful compounds for the treatment of diabetes and as insulin sensitizing agents (*J. Med. Chem.*, 1996, 39, 5053). PCT Patent No. WO 93/13095 describes the use of cobalt ion, a ligand and a reducing agent to convert the final step reduction of 5-methylene thiazolidinedione to saturated analogues.

U.S. Pat. No. 5,594,015 describes the new use of Pioglitazone for the treatment of Psoriasis. Various other strategies to synthesize Pioglitazone are disclosed in Patents EP 0506273. As discussed above in the prior art, the known method to prepare compounds of general formula 1, in particular, Pioglitazone, involves technically difficult procedures to handle bad odour, low temperature diazotization, evolution of large excess of gas and special precautions to handle effluents.

Besides, above mentioned procedures lead to the formation of unwanted impurities, the removal of which is a time consuming process. Environmentally also, it requires evolution of HBr gas, which requires upstream processing and consequent additional cost.

Subsequent to our provisional application a recent published article in *Organic Process Research Development*, 2002, 6, 721-728 describes a method for preparing compound of formula 14, when X=O

OBJECTIVE OF THE INVENTION

The present inventors have examined possibilities to find out processes to overcome the above drawbacks. The main objective of the present invention is to provide novel processes for the manufacture of various pyridine substituted 5-[4-[2-(alkyl substituted pyridyl)ethoxy]benzyl-2,4-thiazolidinedione derivatives, especially Pioglitazone hydrochloride (1, R=5-ethyl). Another objective of the present invention is to report several new and novel intermediates for the manufacture of Pioglitazone hydrochloride.

Above objectives as well as other objectives and advantages of the present invention will become apparent to those skilled in the art, as we go through the following description, especially summary of the invention.

SUMMARY OF THE INVENTION

Accordingly, the present invention provides a new, novel and general process to prepare various pyridine substituted 5-[4-[2-(alkyl substituted pyridyl)ethoxy]benzyl-2,4-thiazolidinedione derivatives of general formula 1, and their pharmaceutically acceptable salts. The present invention especially provides a novel process to prepare Pioglitazone hydrochloride, via novel intermediates. This process involves lesser number of steps with high yield and uses key solid intermediates, which are operationally simple, and therefore offers opportunities for better commercial viability. Some of the novel intermediates described in this invention are 3, 5, 6, 9, 10b, 11, 13 and 14.

Another objective of the present invention is to describe a process for preparation of an intermediate 13 g, R=3-ethyl, X=H (Scheme II) for Pioglitazone hydrochloride 1.

The most preferred objective of the present invention is to describe a process for the manufacture of Pioglitazone 1 (R=3-ethyl), and its pharmaceutically acceptable salts. The preferred method to prepare 1 involves the synthetic sequence 2 to 9 to 13 to 14 to 1 and/or 2 to 9 to 13 to 1.

Scheme I

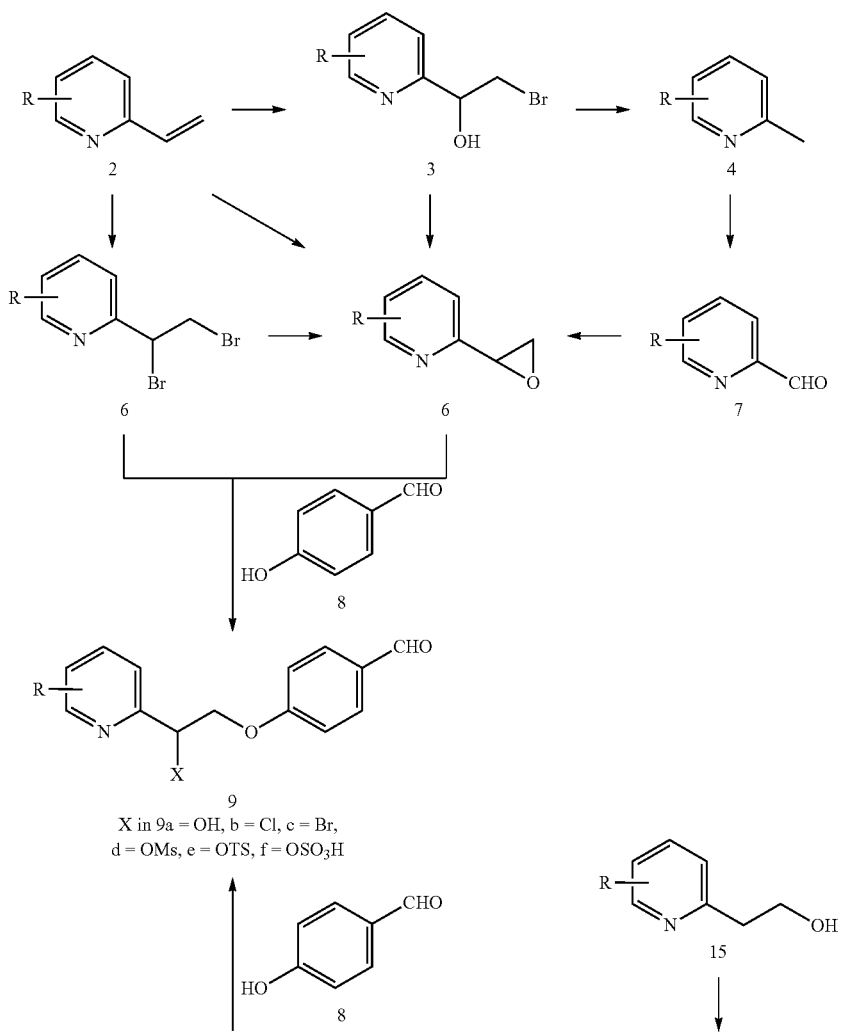

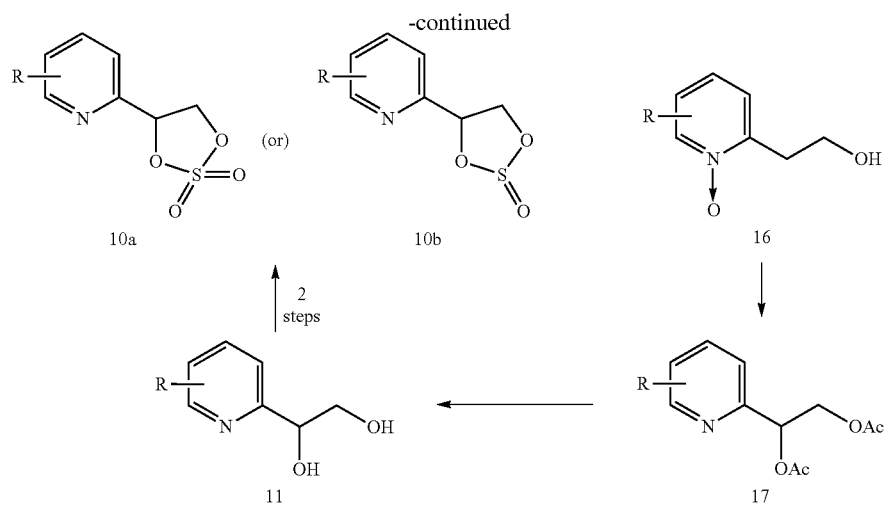
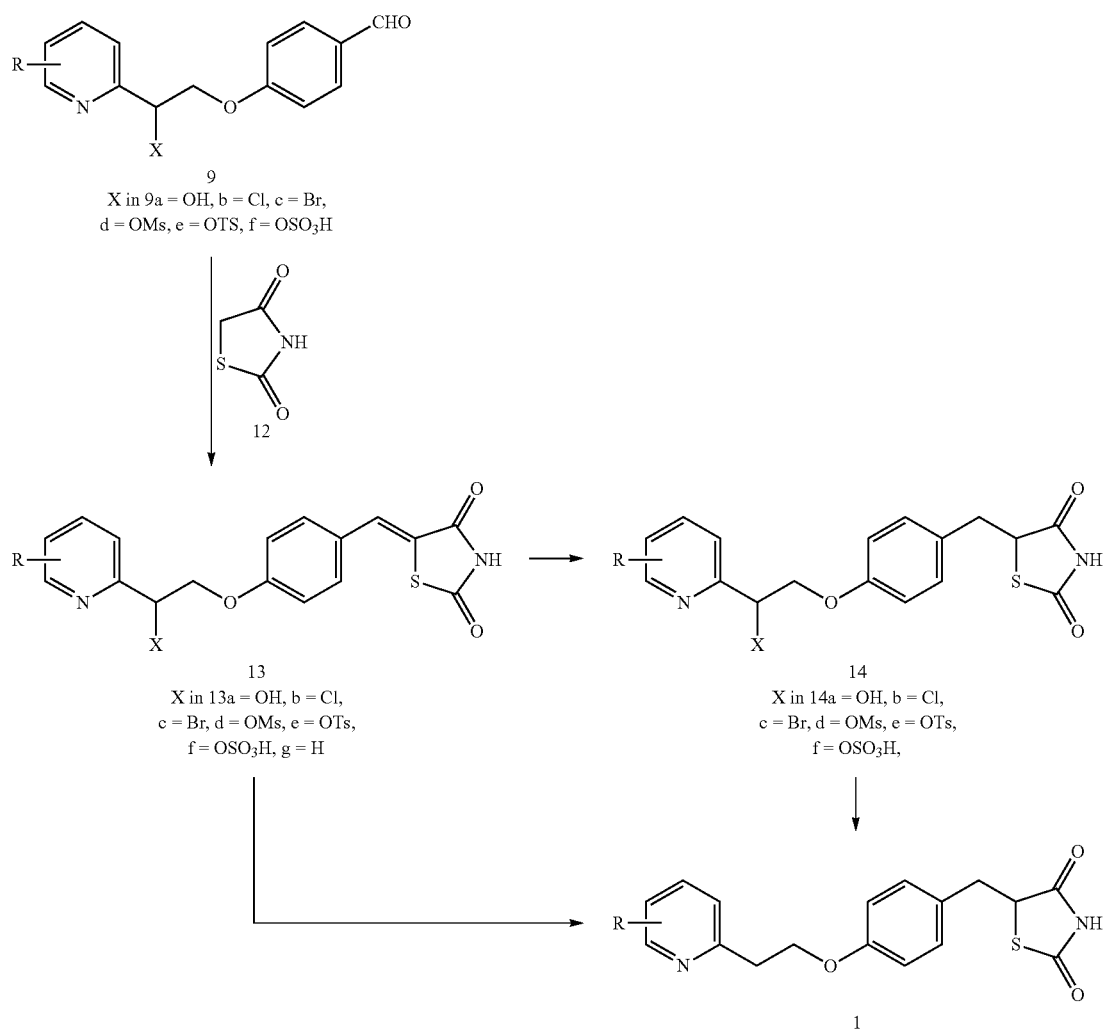
Scheme II

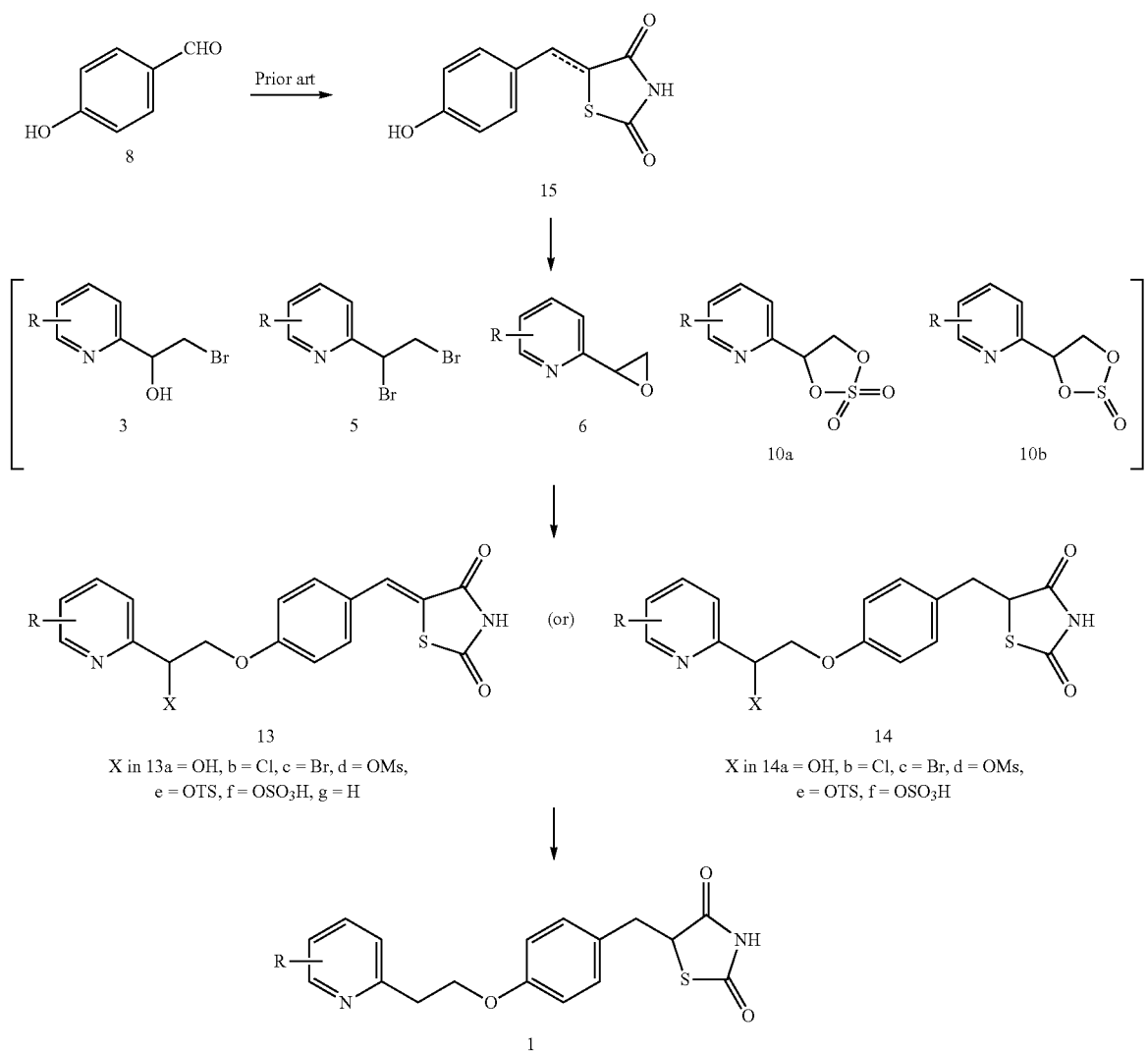

Scheme III

X in 13a = OH, b = Cl, c = Br, d = OMs,
e = OTS, f = OSO₃H, g = H

X in 14a = OH, b = Cl, c = Br, d = OMs,
e = OTS, f = OSO₃H

DETAILED DESCRIPTION OF THE INVENTION

The present invention provides a novel process to prepare substituted 5-[4-[2-(alkyl substituted pyridyl)ethoxy]benzyl-2,4-thiazolidinedione derivatives of general formula 1, and their pharmaceutically acceptable salts. Referring to the general formula 1, where R is denoted by straight chain or branched alkyl group of one to six carbon atoms, such as methyl, ethyl, propyl, iso-propyl, butyl, iso-butyl, sec-butyl, tert-butyl, pentyl, iso-pentyl, neo-pentyl, hexyl etc, more preferably the lower alkyl groups of one to three carbon atoms. Such an alkyl group may be substituted in any position of the pyridine ring. The most preferred substituent and position for R in pyridine is 5-ethyl for Pioglitazone 1.

The starting materials, 2-vinyl-5-ethyl pyridine (2) (R=5-ethyl, Scheme 1) and 5-ethyl-pyridine-2-carboxaldehyde (7), (R=5-ethyl), required for carrying out the multistep synthetic operations involved with this invention are known compounds, which may be easily prepared from commercially available 5-ethyl-2-pyridyl-2-ethanol or 5-ethyl-2-methyl pyridine, by those skilled in the art, using conventional methods.

The synthetic sequence comprises involvement of several novel intermediates eg. 9, 13, 14, 3, 6, 5, 10a and 10b with possibilities of varied substituents in 9, 13 and 14 (X=OH, Cl, Br, OTs, OMs, SO₃H) (Scheme I, II & III). Many of these novel intermediates eg. 9, 13 and 14 are inter convertible. For example, 9a (X=OH) which can be converted into 9b (X=Cl) or to 9d (X=OMs) or to 9e (X=OTs). The most preferred synthetic strategy to prepare 1 involves the synthetic sequence 2 to 9 to 13 to 14 to 1 (Scheme I/II) and/or 2 to 9 to 13 to 1.

The synthesis of novel key intermediate 9 with various substitution patterns eg, 9a X=OH, 4-[2-hydroxy-2-[5-ethyl-pyridyl]ethoxy benzaldehyde; 9b X=Cl, 4-[2-chloro-2-[5-ethylpyridyl]ethoxybenzaldehyde; 9c X=Br, 4-[2-bromo-2-[5-ethylpyridyl]ethoxybenzaldehyde; 9d X=OMs, 4-[2-mesyl-2-[5-ethylpyridyl]ethoxybenzaldehyde; 9e X=OTs, 4-[2-p-tosyl-2-[5-ethylpyridyl]ethoxybenzaldehyde; 9f X=OSO₃H 4-[2-hydroxy sulfonyloxy-2-[5-ethylpyridyl]ethoxybenzaldehyde etc, can be achieved by reacting p-hydroxy benzaldehyde with suitable inorganic base and suitable electrophiles eg. bromohydrin 3, epoxide 6, or dibromide 5, or cyclic sulfate 10a, or cyclic sulfite 10b in suitable solvents. Suitable inorganic bases include but are not limited to sodium carbonate, potassium carbonate, cesium carbonate, sodium hydroxide, potassium hydroxide, sodium hydride, and the like. Suitable polar and neutral solvents for the above transformation include but are not limited to dimethyl sulfoxide, dimethyl formamide, tetrahydrofuran, dimethoxyethane, acetonitrile, toluene, methanol, ethanol, tert-butanol, isopropyl alcohol and the like, in a ratio 3 to 50 volume with respect to the starting material. Occasionally, potassium salt of p-hydroxybenzaldehyde (8) is used to couple with epoxide (6) or cyclic sulfite (10b), under above conditions to prepare 9a. Phase transfer catalysis e.g. PEG-2000, PEG-4000 and 18-C-6 may also be employed for better yield and quality. The usual impurities formed in these reactions are isomeric primary hydroxyaldehyde (see Example 17) and 2-acetyl-5-ethyl pyridine. Alternatively, 2 can be reacted to 8 in one step to give 9c X=Br, via some of the synthetic transformations described in Larrock's book p 642. Preferably, use of N-bromosuccinimide with 2, in the presence of 8, in an inert solvent can give 9c X=Br. Similarly, use of N-chloro-succinimide can lead to 9b, X=Cl in one step.

Several methods can be employed for formation of bromohydrin 3 from vinyl pyridine 2. Suitable methods involve use of N-bromosuccinimide (1 to 3 eq) in a suitable solvent in the presence of at least one equivalent of water. Suitable solvents for bromohydrin 3 formation are dimethyl sulfoxide, acetone, tetrahydrofuran, tert-butanol, dimethoxyethane along with varied proportion of water in a ratio of 3 to 50 volume. Treatment of base e.g. $K_2CO_3$, $Na_2CO_3$, NaOH, KOH with bromohydrin 3 can give the corresponding epoxide 6. The usual impurities formed in this reaction are isomeric bromohydrin and 2-acetyl-5-ethyl pyridine Alternatively, one can also form epoxide 6 directly from olefin 2 via oxidation. Preferably one can couple the bromohydrin formation (2→3) and epoxide formation (3→6) in one step, in an identical manner, as discussed above.

Bromination of olefin 2 with bromine in a neutral solvent e.g. dichloromethane, carbon tetrachloride, can give 5. Similarly, cyclic sulfate 10a may be prepared via oxidation of cyclic sulfite 10b, which in turn may be obtained form diol 11 by reacting with thionyl chloride, in the presence of bases e.g. pyridine, triethylamine. The formation of diol 11, can be achieved from diacetate 17, by treatment with base in water or methanol or ethanol. Alternatively, one can also prepare diol 11, from the diacetate 17 which in turn can be obtained from N-oxide of 5-ethyl-2-pyridyl-2-ethanol as shown in scheme I. In all the above transformations (Scheme 1) upon completion of the reaction, the desired compound is easily isolated from the reaction mixture in a most conventional manner eg. extracting in organic layer, washing with water, drying organic layer, concentrating and purifying/crystallizing the desired final product.

As mentioned earlier, some of the substituents in 9, are interconvertible. Thus, alcohol 9a X=OH, may be transformed to chloride 9b X=Cl by reacting with thionyl chloride in an inert solvent e.g. toluene, dichloro methane, chloroform. Similarly, bromide 9c X=Br, can be obtained by treating alcohol 9a X=OH with $PBr_3$. Tosylation (9e X=OTs) of alcohol 9a X=OH, is achieved by reacting with TosCl (p-toluene sulfonyl chloride) in the presence of an organic or inorganic base. Similarly, mesylated compound 9d X=OMs, may be prepared by reacting alcohol 9a X=OH with mesyl chloride (methane sulfonyl chloride) in the presence of a base.

The condensation of variously substituted aromatic aldehyde 9a-e with 5-20% excess molar ratio of 2,4-thiazolidinedione 12 is accomplished by azeotropic removal of water in a suitable solvent and in the presence of an organic base and catalytic amount of organic acid. Suitable organic bases include, but are not limited to ammonia, methyl amine, ethyl amine, n-butyl amine, pyrrolidine, piperidine, pyridine, morpholine, piperazine, diethylamine, di-isopropyl amine, triethyl amine and the like; whereas suitable catalytic acids include, but are not limited to acetic acid, benzoic acid, p-tolune sulfonic acid, hydrochloric acid, hydrobromic acid and the like. Suitable organic solvents for such condensation include, but are not limited to methanol, ethanol, propanol, 2-propanol, butanol, iso-butanol, 2-methoxyethanol, dimethyl formamide, dimethyl sulfoxide, sulfolane, acetonitrile, dioxalane, dimethoxyethane, toluene, acetic acid and the like.

The chemoselective reduction of 13a-e (X=OH, Cl, Br, OMs, OTs) to 14a-e (X=OH, Cl, Br, OMs, OTs) is accomplished by usual double bond reducing methodologies described in R. C. Larrock, "Comprehensive Organic Transformations", John Wiley & Sons, Inc, 1999, $2^{nd}$ Ed, (herein referred to as Larrock's book) p 7-8, In particular, conversion of 13a (X=OH) to 14a (X=OH) is achieved by reducing with metal borohydrides in a suitable solvent, in the presence of a cobalt catalyst and a ligand. Suitable solvents, include but are not limited to methanol, ethanol, iso-propanol, acetone, dimethyl formamide (DMF) and tetrahydrofuran. Suitable cobalt catalyst include $CoCl_2$ (Cobaltous chloride), $Co(OAc)_2$ (Cobaltous acetate) or $CoCl_3$ (Cobaltic chloride). Some of the ligands useful for this transformation are 2,2'-bipyridyl, 1,10-phenanthroline and dimethyl glyoxime. Sodium borohydride is the preferred reducing agent, but other borohydrides such as lithium borohydride, potassium borohydride, tetraalkylammonium borohydride or Zinc borohydride can also be used. The approximate molar ratio of sodium borohydride, dimethyl glyoxime and cobaltous chloride with respect to the starting material was 3 to 4:0.4 to 0.6:0.05 to 0.2.

Alternatively, chemoselective reduction of 13 to 14 is accomplished under catalytic reduction conditions in a suitable solvent in the presence of a suitable catalyst. Suitable solvents include but are not limited to alkanols such as methanol, ethanol, propanol etc; ethers such as dioxane, dimethoxyethane, tetrahydrofuran, and other miscellaneous solvents eg. ethyl acetate, acetic acid, dimethyl formamide, N-methyl pyrrolidine, either alone or in combinations thereof. Suitable catalysts employed in this transformation include, but are not limited to palladium black, palladium charcoal, palladium on barium sulfate, palladium on barium carbonate, platinum oxide, platinum on carbon, Raney Nickel and the like.

By varying experimental conditions in the above two reducing conditions eg. alkali metal borohydrides and catalytic hydrogenation conditions, the transformation from 13 to 14 and finally 14 to 1 may be accomplished in one step, especially if the substituents in 13 are X=Cl, Br, OTs, OMs. Usually, 3 to 10 molecular equivalents of metal borohydrides mentioned above, and high reflux temperature are required to accomplish both transformations in one step.

For deoxygenation of 13a or 14a (X=OH), to 1 (X=H), triethyl silane induced reduction in the presence of a suitable protic acids are advantageous. Some of the protic acids used include, but are not limited to conc. sulfuric acid, acetic acid, triflic acid, Nafion-H, trifluoroacetic acid and the like. Alternatively, deoxygenation with $AlCl_3$ in the presence of 10% Pd—C and cyclohexene as hydrogen donor is also possible. There are several other useful methods described in Larrock's book p 44-45, to accomplish similar transformations and any one of them may be advantageously used, so long as they achieve our objectives.

The transformation of 14b-e (X=Cl, Br, OMs, OTs) or its salts to 1 may also be achieved by reacting with zinc (molar ratio 0.5 to 2 w.r.t. 14) in acetic acid or propionic acid or HCl, under reflux conditions, or Raney nickel or 10% Pd—C in a suitable solvent like MeOH, EtOH, isopropanol, $H_2O$, THF and the like or their mixtures thereof, optionally in presence of additives like $NH_4Cl$, TMEDA and the like. The usual impurities formed in the reaction are ether cleavage products e.g. 5-ethyl-2-vinyl pyridine 2 and 15. Subsequently the suitable salt of 1 preferably HCl salt can be prepared in methanol, ethanol, isopropanol and the like Alternatively, the useful intermediates 13a-f or 14a-g may also be obtained by reacting the key intermediates 3, 5, 6, 10a and 10b with another advanced intermediate unsaturated benzylidene type 15 or saturated para-hydroxybenzyl substituted thiazolidinedione 15, known in prior art, in the presence of a base (Scheme III), similar to as described above for nucleophilic attack of p-hydroxy benzaldehyde 8 to the above key intermediates 3, 5, 6, 10a and 10b (Scheme I). The reagents, solvents and reaction condition can be advantageously utilized, as described earlier for similar transformation.

The various novel intermediates 3, 5, 6, 9, 10b, 11, 13 and 14 described in the present invention may be converted to corresponding salts by procedures known in prior art. For example, with pyridine ring in these intermediates, they can be converted to acid addition salts with acids such as tartaric acid, mandelic acid, fumaric acid, malic acid, lactic acid, maleic acid, salicylic acid, citric acid, ascorbic acid, benzene sulfonic acid, p-toluene sulfonic acid, hydroxynaphthoic acid, methane sulfonic acid, acetic acid, benzoic acid, succinic acid, palmitic acid, hydrochloric acid, hydrobromic acid, sulfuric acid, nitric acid and the like in solvents such as water, alcohols, ethers, ethyl acetate, dioxane, THF, acetonitrile, DMF or a lower alkyl ketone such as acetone, or mixtures thereof. Many of these salts are solids and offer operational simplicity for purification and manufacturing. Similarly, thiazolidinediones in 13 and 14 can be converted to their corresponding cationic salts such as sodium ion, potassium ion, calcium ion or an ammonium ion and the like.

The process described in the present invention is demonstrated in the examples illustrated below. These examples are provided as illustration and should not be considered as limiting the scope of invention in any way. In all these examples R=5-ethyl, and X is indicated in the titles of examples.

EXAMPLE 1

2-Bromo-1-(5-ethyl pyridin-2-yl)-ethanol (3)

To a stirred mixture of 225 mL, 1,4-dioxane and 225 mL water, 75 g (0.5639 mol) of 5-ethyl-2-vinyl-pyridine was added, followed by 149 g (0.8371 mol) N-bromosuccinimide was added in to it. Reaction mixture was stirred at 25-30° C. for 4 hr. and subsequently quenched with excess water. Product was extracted with dichloromethane. Organic layer was separated and dried over calcium chloride. On concentrating the organic layer and purifying the residue, it gave 110.24 g (85%) of desired product.

The product obtained was characterized by IR, Mass, $^{13}C$ NMR, and $^1H$ NMR, which are as given below.

IR spectrum ($cm^{-1}$): 3200 (O—H str.), 1085 (C—O Str.), 715 (C—Br str.)

Mass spectrum (m/z): 230.1 $(M)^+$ $^{13}C$-NMR (DMSO-$d_6$): δ 153.38, 145.33, 142.35, 140.40, 124.40, 68.29, 38.11, 24.60, 14.56

$^1H$-NMR (DMSO-$d_6$): δ 8.03-8.68 (3H, m), 5.37 (1H, t), 3.91 (2H, d), 2.76 (2H, q), 1.22 (3H, t)

EXAMPLE 2

2-Bromo-1-(5-ethyl pyridin-2-yl)-ethanol (3)

To a solution at −5° C., of 50 g (0.3759 mol) 5-ethyl-2-vinyl-pyridine dissolved in a mixture of 2504 mL dimethyl-sulfoxide and 13.5 mL water was added 99.3 g (0.5578 mole) N-bromosuccinimide and stirring was continued for 30 min. at 0 to −5° C. Reaction mixture was quenched with 2500 mL water and the product was extracted with dichloromethane. Organic layer was dried (calcium chloride); concentrated and purified to get the desired product. Yield of the product was 76.09 g (88%). The two side products in this reaction found were 2-acetyl-5-ethyl-pyridine (5%) and 2-(1-bromo vinyl)-5-ethyl-pyridine (6%).

The product obtained was characterized by IR, Mass, $^{13}C$ NMR and $^1H$ NMR, which was found to be identical with the product obtained in example 1.

EXAMPLE 3

2-Bromo-1-(5-ethyl pyridin-2-yl)-ethanol (3)

5.5 g (0.0344 mol) liq. Bromine was added to a solution of 7.83 g (0.0658 mol) KBr dissolved in 100 mL water. Reaction mixture was heated to 60-65° C. and 5 g (0.0376 mol) of 5-ethyl-2-vinyl-pyridine was added into it in 10 min. Reaction mixture was stirred for 30 min. and quenched with excess of water. Product was extracted with dichloromethane, which was separated, dried, concentrated and purified to get 7.43 g (86%) of the titled product.

The product obtained was characterized by IR, Mass, $^{13}C$ NMR and $^1H$ NMR, which was found to be identical with the product obtained in example 1.

EXAMPLE 4

2-Bromo-1-(5-ethyl pyridin-2-yl)-ethanol (3)

The procedure described in example 1 was repeated, except that tetrahydrofuran was used as solvent, and substantially the same results were achieved. In this particular case, the final product 2-bromo-1-(5-ethyl pyridin-2-yl)-ethanol obtained was 106.35 g (82%), is identical in every respect with the product of example 1.

EXAMPLE 5

2-Bromo-1-(5-ethyl pyridin-2-yl)-ethanol (3)

Into 75 mL 25% aqueous tertiary butanol, 5 g (0.0372 mol) 5-ethyl-2-vinyl-pyridine was added, followed by the addition of 8 g (0.0446 mole) N-bromosuccinimide in 10 min. Reaction mixture was stirred at 25 to 30° C. for 1 hr. and quenched with excess water. Product was extracted with dichloromethane. Organic layer was dried (calcium chloride), concentrated and the residue obtained was purified to obtain 8.21 g (95%) of the desired product. The impurity profile in this reaction was similar to the impurity profile described in example 2.

The product obtained was characterized by IR, Mass, $^{13}C$ NMR and $^1H$ NMR, which was found to be identical with the product obtained in example 1.

EXAMPLE 6

2-Bromo-1-(5-ethyl pyridin-2-yl)-ethanol (3)

The procedure described in example 5 was repeated except that 5% aqueous tertiary butanol was used as solvent, and substantially the same results were achieved. In this particular case, the final product 2-bromo-1-(5-ethyl pyridin-2-yl)-ethanol obtained was 8.04 g (93%), is identical in every respect with the product of example 1.

EXAMPLE 7

5-Ethyl-2-oxiranyl-pyridine (6)

To a stirred solution of 10 g (0.0426 mol) of 2-bromo-1-(5-ethyl pyridin-2-yl)-ethanol dissolved in 50 mL of methanol, 6.86 g (0.0511 mol) potassium carbonate was added at 25-30° C. and stirring was continued for 1 hr. Subsequently filtered and methanol was concentrated to furnish 5.8 g (90%) of the desired product.

The product obtained was characterized by IR, Mass, $^{13}$C NMR and $^1$H NMR, which are as given below.

IR spectrum (cm$^{-1}$): 2875, 2972 (saturated C—H str.), 987 (C—O—C str.)

Mass spectrum (m/z): 150.1 (M+H)$^+$ $^{13}$C-NMR (CDCl$_3$): δ 154.35, 149.04, 138.80, 136.08, 119.0, 63.61, 50.16, 25.76, 15.23

$^1$H NMR (CDCl$_3$): δ 7.14-8.41 (3H, m), 3.98 (1H, d), 2.94-3.16 (2H, m), 2.68 (2H, q), 1.26 (3H, t)

EXAMPLE 8

5-Ethyl-2-oxiranyl-pyridine (6)

The procedure described in example 7 was repeated except that 25% aqueous tert-butanol was used as solvent, and substantially the same results were achieved. In this particular case, the final product 5-ethyl-2-oxiranyl-pyridine obtained was 6.34 g (98%), is identical in every respect with the product of example 7.

EXAMPLE 9

5-Ethyl-2-oxiranyl-pyridine (6)

The procedure described in example 7 was repeated except that isopropyl alcohol was used as solvent, and substantially the same results were achieved, in this particular case, the final product 5-ethyl-2-oxiranyl-pyridine obtained was 5.89 g (91%), is identical in every respect with the product example 7.

EXAMPLE 10

5-Ethyl-2-oxiranyl-pyridine (6)

The procedure described in example 7 was repeated, except that dimethylsulfoxide was used as solvent, and substantially the same results were achieved. In this particular case, the final product 5-ethyl-2-oxiranyl-pyridine obtained was 6.02 g (93%), is identical in every respect with the product of example 7.

EXAMPLE 11

5-Ethyl-2-oxiranyl-pyridine (6)

The procedure described in example 7 was repeated, except that 2% aqueous dimethylsulfoxide was used as solvent, and substantially the same results were achieved. In this particular case, the final product 5-ethyl-2-oxiranyl-pyridine obtained was 6.02 g (93%), is identical in every respect with the product of example 7.

EXAMPLE 12

5-Ethyl-2-oxiranyl-pyridine (6)

The procedure described in example 7 was repeated, except that toluene was used as solvent, and substantially the same results were achieved. In this particular case, the final product 5-ethyl-2-oxiranyl-pyridine obtained was 5.96 g (92%), is identical in every respect with the product of example 7.

EXAMPLE 13

5-Ethyl-2-oxiranyl-pyridine (6)

The procedure described in example 7 was repeated, except that 1.02 g (0.0426 mol) sodium hydride was used as base, and substantially the same results were achieved. In this particular case, the final product 5-ethyl-2-oxiranyl-pyridine obtained was 6.02 g (93%), is identical in every respect with the product of example 7.

EXAMPLE 14

5-Ethyl-2-oxiranyl-pyridine (6)

The procedure described in example 7 was repeated, except that 1.7 g (0.0426 mol) sodium hydroxide was used as base, and substantially the same results were achieved. In this particular case, the final product 5-ethyl-2-oxiranyl-pyridine obtained was 5.83 g (90%), is identical in every respect with the product of example 7.

EXAMPLE 15

5-Ethyl-2-oxiranyl-pyridine (6)

To a mixture of 750 mL tert-butanol and 2250 mL water, 200 g (1.488 mol) of 5-ethyl-2-vinyl-pyridine was dissolved and under stirring 324 g (1.786 mol) N-bromosuccinimide was added in 30 min. at 25-30° C. Stirring was continued for 1 hr. and 178.6 g (4.46 mol) of NaOH dissolved in 2250 mL water was added into it. Reaction mixture was stirred for 45 min. Product was extracted twice with 1100 mL methyl tert-butyl ether. Organic layers were combined, washed with brine, dried over magnesium sulfate and concentrated in vacuo to yield 206.13 g (92%) of 6.

The product obtained was characterized by IR, Mass, $^{13}$C NMR and $^1$H NMR is identical in every respect with the product of example 7.

EXAMPLE 16

5-Ethyl-2-oxiranyl-pyridine (6)

To a stirred solution of 400 g (2.974 mol) 5-ethyl-2-vinyl-pyridine dissolved in a mixture of 1000 mL of dimethyl sulfoxide and 106 mL water, was added 741.9 g (4.16 mol) N-bromosuccinimide at 0 to −5° C. Reaction mixture was stirred for 1 hr. The progress of reaction was monitored by TLC and after complete consumption of 5-ethyl-2-vinyl-pyridine, 833 g (6.015 mol) of K$_2$CO$_3$ along with 400 mL methanol was added at 25-30° C. Stirring was continued for 1 hr. and after subsequent work-up 358.49 g (80%) of the desired product was obtained.

The product obtained was characterized by IR, Mass, $^{13}$C NMR and $^1$H NMR, which was found to be identical with the product obtained in example 7.

EXAMPLE 17

4-[2-(5-Ethyl-pyridin-2-yl)-2-hydroxy-ethoxy]-benzaldehyde (9a)

11.35 g (0.283 mol) of sodium hydride in 10 mL dimethylformamide was added into a solution of 19.27 g (0.158 mol) of 4-hydroxy benzaldehyde dissolved in 100 mL dimethylformamide and stirred for 5 min. To this was added 30 g (0.129 mol) of 2-bromo-1-(5-ethyl-pyridin-2-yl)-ethanol dissolved in 1000 mL dimethylformamide slowly and stirring was continued for 1 hr. at 25 to 30° C. Reaction mixture was heated at 80 to 90° C. for 14 hr., cooled to 25° C. and poured in excess of water. Product was extracted with diethyl ether. Diethyl ether layer was dried (magnesium sulfate) and concentrated to obtain 30.04 g (85%) of crude product.

The crude product was suspended in 140 mL diisopropyl ether and refluxed at 70° C. with charcoal. After filtration and cooling 24.03 g (68%) purified 4-[2-(5-ethyl-pyridin-2-yl)-2-hydroxy-ethoxy]-benzaldehyde was separated and 5.1 g (14.4%) of its regioisomer was also obtained.

The product obtained was characterized by IR, Mass, $^{13}$C NMR and $^1$H NMR, which are as given below.

IR spectrum (cm$^{-1}$): 1701 (C=O str.), 3413 (O—H str.)
Mass spectrum (m/z): 272.2 (M+H)$^+$
$^{13}$C-NMR (CDCl$_3$): δ 190.75, 163.52, 155.53, 148.02, 138.70, 136.26, 131.84, 129.96, 120.73, 114.79, 72.48, 71.15, 25.65, 15.19
$^1$H-NMR (CDCl$_3$): δ 9.85 (1H, s), 6.98-8.41 (7H, m), 5.14 (1H, t), 4.5 (1H, brs), 4.28 (2H, d), 2.67 (2H, q), 1.25 (3H, t)
Melting point: 80-83° C.

The regioisomer 4-[1-(5-ethyl-pyridin-2-yl)-2-hydroxy-ethoxy]-benzaldehyde of the titled product separated was a low melting solid and was characterized by IR, Mass, $^{13}$C NMR and $^1$H NMR, which are as given below.

IR spectrum (cm$^{-1}$) 1683 (C=O str.), 3475 (O—H str.)
Mass spectrum (m/z): 272.1 (M+H)$^+$
$^{13}$C-NMR (CDCl$_3$): δ 191.1, 162.9, 154.7, 148.7, 138.3, 136.1, 131.7, 129.6, 120.9, 114.6, 72.1, 65.6, 24.9, 15.1
$^1$H-NMR (CDCl$_3$): δ 9.79 (1H, s), 7.05-8.43 (7H, m), 5.45 (1H, t), 3.84 (2H, d), 2.67 (2H, q), 1.20 (3H, t)

EXAMPLE 18

4-[2-(5-Ethyl-pyridin-2-yl)-2-hydroxy-ethoxy]-benzaldehyde (9a)

Into a solution of 2.9 g (0.0234 mol) of 4-hydroxy benzaldehyde dissolved in 100 mL dimethylformamide, 8.94 g (0.063 mol) of potassium carbonate in 20 mL dimethylformamide was added in 10 min. followed by slow addition of 5 g (0.0213 mol) of 2-bromo-1-(5-ethyl-pyridin-2-yl)-ethanol dissolved in 1000 mL dimethylformamide. Reaction mixture was stirred for 1 hr. at 25 to 30° C., heated at 80 to 90° C. for 14 hr. and poured into excess of water at 25° C. Product was extracted with diethyl ether. Subsequent concentration in vacuo of the organic layer and purification as described earlier yielded 3.97 g (67.5%) of the desired product. m.p. 80° C.

The product obtained was characterized by IR, Mass, $^{13}$C NMR and $^1$H NMR, which was found to be identical with the product obtained in example 17.

EXAMPLE 19

4-[2-(5-Ethyl-pyridin-2-yl)-2-hydroxy-ethoxy]-benzaldehyde (9a)

Into a solution of 22.6 g (0.181 mol) of 4-hydroxy benzaldehyde dissolved in 75 mL tertiary butanol, was added 38.5 g (0.278 mol) of potassium carbonate in 10 min. Reaction mixture was refluxed for 1 hr. and 15 g (0.06 mol) of 2-bromo-1-(5-ethyl-pyridin-2-yl)-ethanol dissolved in 75 mL tertiary butanol was added slowly in one hr. Reaction mixture was refluxed further for 10 hr, and at 25° C. poured into excess of water. Product was extracted with toluene. Subsequent concentration under reduced pressure and purification gave the desired product. Yield of the product was 12.37 g (70%). m.p. 80° C.

The product obtained was characterized by IR, Mass, $^{13}$C NMR, and $^1$H NMR, which was found to be identical with the product obtained in example 17.

EXAMPLE 20

4-[2-(5-Ethyl-pyridin-2-yl)-2-hydroxy-ethoxy]-benzaldehyde (9a)

The procedure described in example 19 was repeated except that isopropyl alcohol was used as solvent, and substantially the same results were achieved. In this particular case, the final 4-[2-(5-ethyl-pyridin-2-yl)-2-hydroxy-ethoxy]-benzaldehyde obtained was 11.49 g (65%), is identical in every respect with the product of example 17. m.p. 81° C.

EXAMPLE 21

4-[2-(5-Ethyl-pyridin-2-yl)-2-hydroxy-ethoxy]-benzaldehyde (9a)

The procedure described in example 19 was repeated except that methanol was used as solvent, and substantially the same results were achieved. In this particular case, the final 4-[2-(5-ethyl-pyridin-2-yl)-2-hydroxy-ethoxy]-benzaldehyde obtained was 11.31 g (64%), is identical in every respect with the product of example 17. m.p. 82° C.

EXAMPLE 22

4-[2-(5-Ethyl-pyridin-2-yl)-2-hydroxy-ethoxy]-benzaldehyde (9a)

The procedure described in example 19 was repeated except that dimethylsulfoxide was used as solvent, and substantially the same results were achieved. In this particular case, the final 4-[2-(5-ethyl-pyridin-2-yl)-2-hydroxy-ethoxy]-benzaldehyde obtained was 12 g (68%), is identical in every respect with the product of example 17 m.p. 83° C.

EXAMPLE 23

4-[2-(5-Ethyl-pyridin-2-yl)-2-hydroxy-ethoxy]-benzaldehyde (9a)

The procedure described in example 19 was repeated except that toluene was used as solvent, and substantially the same results were achieved. In this particular case, the final 4-[2-(5-ethyl-pyridin-2-yl)-2-hydroxy-ethoxy]-benzaldehyde obtained was 10.6 g (60%), is identical in every respect with the product of example 17. m.p. 80° C.

EXAMPLE 24

4-[2-(5-Ethyl-pyridin-2-yl)-2-hydroxy-ethoxy]-benzaldehyde (9a)

Into a solution of 9.635 kg (72.99 mol) of 4-hydroxy benzaldehyde dissolved in 50 lit. dimethylformamide was added 5.675 kg (236.45 mol) of sodium hydride in 5 lit. dimethylformamide and stirred for 15 min. To this was added 15 Kg (65.22 mol) of 2-bromo-1-(5-ethyl pyridin-2-yl)-ethanol dissolved in 500 lit dimethylformamide and stirring was continued for 1 hr. at 25 to 30° C. Reaction mixture was heated at 80 to 90° C. for 14 hr., allowed to cool to 25° C. and excess of water was added into it. Product was extracted with diethyl ether. Organic layer was dried (magnesium sulfate) and concentrated to obtain crude product, which was purified in methyl tert-butyl ether as described in example 17 to obtain 12.195 Kg (69%) pure 4-[2-(5-ethyl-pyridin-2-yl)-2-hydroxy-ethoxy]-benzaldehyde. m.p. 83° C.

The impurity profile in this reaction was similar to the impurity profile of example 17.

EXAMPLE 25

4-[2-(5-Ethyl-pyridin-2-yl)-2-hydroxy-ethoxy]-benzaldehyde (9a)

To a flask fitted with an overhead stirrer, a thermometer and a condensor was added 500 g (3.759 mol) 5-ethyl-2-vinyl-pyridine dissolved in 7500 mL of 25% aqueous tertiary butanol. To this was added 802 g (4.5 mol) N-bromosuccinimide at 25-30° C. in 30 min. Reaction mixture was stirred for 2 hr. The progress of reaction was monitored by TLC and after complete consumption of the 5-ethyl-2-vinyl-pyridine, 762 g (5.52 mol) of $K_2CO_3$ was added in one lot along with 537 g (4.4 mol) 4-hydroxy benzaldehyde. Reaction mixture was stirred for 18 hr. at 75-80° C. Subsequent work-up in water, extraction with ethyl acetate and purification yielded 805 g (79%) of the titled product. m.p. 83° C.

The product obtained was characterized by IR, Mass, $^{13}C$ NMR and $^1H$ NMR, which was found to be identical with the product obtained in example 17. The impurity profile in this reaction was similar to the impurity profile of example 17.

EXAMPLE 26

4-[2-(5-Ethyl-pyridin-2-yl)-2-hydroxy-ethoxy]-benzaldehyde (9a)

To a flask fitted with an overhead stirrer, a thermometer and a condensor was added a solution of 12 Kg (90.22 mole) 5-ethyl-2-vinyl-pyridine dissolved in a mixture of 45 lit. tert-butanol and 135 lit. water at 25° C., followed by addition of 19.26 Kg (108.25 mole) N-bromosuccinimide and reaction mixture was stirred for 1.5 hr, 135 lit. aqueous 2N NaOH solution was added to the reaction mixture and stirring was continued for further 45 min. Progress of reaction was monitored by TLC and after completion of reaction, product was extracted with 120 lit. methylene chloride. Layers were separated, organic layer was washed with 72 lit. brine solution, dried (magnesium sulfate) and concentrated under reduced pressure. The residual mass obtained was added into a stirred mixture of 15.96 Kg (130.8 mole) 4-hydroxy benzaldehyde dissolved in 130 lit. toluene and 5.23 Kg (1307 mole) NaOH dissolved in 120 lit. water. To this was added 2.21 Kg PEG 4000 and stirred for 17 hr. at 78° C. Subsequent work-up gave 20.538 Kg (84%) 4-[2-(5-ethyl-pyridin-2-yl)-2-hydroxy-ethoxy]-benzaldehyde. m.p. 82° C.

The product obtained was characterized by IR, Mass, $^{13}C$ NMR and $^1H$ NMR, which was found to be identical with the product obtained in example 17. The impurity profile in this reaction was similar to the impurity profile of example 17.

EXAMPLE 27

4-[2-(5-Ethyl-pyridin-2-yl)-2-hydroxy-ethoxy]-benzaldehyde (9a)

Into a stirred mixture of 4.5 lit. tert-butanol and 13.5 lit. water was added 1.2 Kg (9.02 mole) 5-ethyl-2-vinyl-pyridine at 25° C. To this was added 1.926 Kg (10.82 mol) N-bromosuccinimide and reaction mixture was stirred for 1.5 hr. 13.5 lit. aqueous 2N NaOH solution was added to the reaction mixture and stirring was continued for further 45 min. Progress of reaction was monitored by TLC and after completion of reaction, product was extracted with 12 lit. methyl tert-butyl ether. Layers were separated, organic layer was washed with 7.2 lit. brine solution, dried (magnesium sulfate) and concentrated under reduced pressure. The residual solid obtained was added into a stirred mixture of 1.59 Kg (13 mol) 4-hydroxy benzaldehyde dissolved in 13 lit. toluene and 523 g (130 mol) NaOH dissolved in 120 lit. water. To this was added 221 g PEG 2000 and stirred for 17 hr. at 78° C. Subsequent work-up gave 2.029 Kg (83%) 4-[2-(5-ethyl-pyridin-2-yl)-2-hydroxy-ethoxy]-benzaldehyde, m.p. 81° C.

The product obtained was characterized by IR, Mass, $^{13}C$ NMR and $^1H$ NMR, which was found to be identical with the product obtained in example 17. The impurity profile in this reaction was similar to the impurity profile of example 17.

EXAMPLE 28

4-[2-(5-Ethyl-pyridin-2-yl)-2-hydroxy-ethoxy]-benzaldehyde (9a)

To a solution of 5 g (0.03759 mol) 5-ethyl-2-vinyl-pyridine dissolved in 75 mL of 25% aqueous tertiary butanol added 8.02 g (0.045 mol) N-bromosuccinimide at 25-30° C. in 30 min. Reaction mixture was stirred for 2 hr. The progress of reaction was monitored by TLC and after complete consumption of the 5-ethyl-2-vinyl-pyridine, 6.01 g (0.03759 mol) potassium salt of 4-hydroxy benzaldehyde was added. Reaction mixture was stirred for 18 hr. at 75-80° C. Subsequent work-up in water and extraction with ethyl acetate yielded 8.04 g (79%) of the titled product. m.p. 81° C.

The product obtained was characterized by IR, Mass, $^{13}C$ NMR and $^1H$ NMR, which was found to be identical with the product obtained in example 17.

EXAMPLE 29

4-[2-(5-Ethyl-pyridin-2-yl)-2-hydroxy-ethoxy]-benzaldehyde (9a)

To a mixture of 690 mL tert-butanol and 2075 mL water, 184.46 g (1.3869 mol) of 5-ethyl-2-vinyl-pyridine was dissolved and under stirring 298.83 g (1.6788 mol) N-bromosuccinimide was added in 30 min. at 25-30° C. Stirring was continued for 1 hr. and 164.7 g (4.117 mol) of NaOH dissolved in 2075 mL water was added into it. Reaction mixture was stirred for 45 min and extracted twice with 1000 mL methyl tert-butyl ether. Organic layers were combined, washed with brine, dried over magnesium sulfate and concentrated in vacuo to yield 190 g residual mass. The concentrated product obtained was added to a stirred mixture of 76 g (1.817 mol) NaOH dissolved in 1800 mL water and 223 g (1.817 mol) 4-hydroxy benzaldehyde dissolved in 1900 mL toluene. To this was added 16.65 g (0.063 mol) 18 Crown-6 and stirred for 24 hr. at 78° C. Subsequent work-up yielded 304.44 g (81%) 4-[2-(5-ethyl-pyridin-2-yl)-2-hydroxy-ethoxy]benzaldehyde. m.p. 83° C.

The product obtained was characterized by IR, Mass, $^{13}C$ NMR and $^1H$ NMR, which was found to be identical with the product obtained in example 17. The impurity profile in this reaction was similar to the impurity profile of example 17.

EXAMPLE 30

5-{4-[2-(5-Ethyl-pyridin-2-yl)-2-hydroxy-ethoxy]-benzylidene}-2,4-thiazolidene dione (13, X=OH)

Into 50 mL methanol, 10 g (0.0369 mol) 4-[2-(5-ethyl-pyridin-2-yl)-2-hydroxy-ethoxy]-benzaldehyde, 4.33 g (0.0369 mol) thiazolidin-2,4-dione, 0.43 mL (0.0099 mol) acetic acid, and 0.726 mL (0.0099 mol) piperidine were dissolved. Reaction mixture was refluxed for 4 hr and cooling gave 12 g (88%) of the desired product.

The product obtained was characterized by IR, Mass, $^{13}C$ NMR, and $^1H$ NMR, which are as given below.

IR spectrum (cm$^{-1}$): 3500 (O—H str.), 1701, 1735 (C=O str.), 1037 (C—O—C str.)

Mass spectrum (m/z): 371 (M+H)$^+$ $^{13}$C-NMR (DMSO-d$_6$): δ 167.98, 167.49, 160.38, 158.36, 148.0, 137.65, 135.90, 132.07, 131.79, 125.49, 120.61, 120.29, 115.47, 72.47, 71.82, 25.02, 15.40

$^1$H-NMR (DMSO-d$_6$): δ 12.5 (1H, s), 7.01-8.32 (7H, m), 7.63 (1H, s), 5.80 (1H, s), 4.93 (1H, s), 4.1 (1H, dd), 4.3 (1H, dd), 2.64 (2H, q), 1.20 (3H, t)

Melting point: 158-160° C.

EXAMPLE 31

5-{4-[2-(5-Ethyl-pyridin-2-yl)-2-hydroxy-ethoxy]-benzylidene}-2,4-thiazolidene dione (13, X=OH)

To a stirred solution of 20 g (0.0738 mol) of 4-[2-(5-ethyl-pyridin-2-yl)-2-hydroxy-ethoxy]-benzaldehyde, 8.66 g (0.0738 mol) thiazolidin-2,4-dione in 80 mL toluene, 0.86 (0.0198 mol) mL acetic acid and 1.45 mL (0.0198 mol) piperidine were added. Reaction mixture was refluxed for 2 hr. at 110° C. Water was removed azeotropically. The crude product was purified by addition of isopropyl alcohol to yield 22.11 g (81%) yellow powdered desired product. m.p. 160° C.

The product obtained was characterized by IR, Mass, $^{13}C$ NMR, and $^1H$ NMR, which was found to be identical with the product obtained in example 30.

EXAMPLE 32

5-{4-[2-(5-Ethyl-pyridin-2-yl)-2-hydroxy-ethoxy]-benzylidene}-2,4-thiazolidene dione (13, X=OH)

0.29 mL (0.005 mol) acetic acid and 0.49 mL (0.005 mol) piperidine were added into a mixture of 13.58 g (0.05 mol) 4-[2-(5-ethyl-pyridin-2-yl)-2-hydroxy-ethoxy]-benzaldehyde and 5.9 g (0.05 mol) thiazolidin-2,4-dione, dissolved in 52 mL toluene. Reaction mixture was refluxed for 2 hr. at 110° C. Water was removed azeotropically. After removal of the water, sticky mass separated out from reaction mixture. 35 mL of isopropyl alcohol was added to reaction mixture at 60-70° C. and it was cooled to 25° C. Precipitated product was filtered off and dried to obtain 15.57 g (84%) of the titled product. m.p. 158° C.

The product obtained was characterized by IR, Mass, $^{13}C$ NMR, and $^1H$ NMR, which was found to be identical with the product obtained in example 30.

EXAMPLE 33

5-{4-[2-(5-Ethyl-pyridin-2-yl)-2-hydroxy-ethoxy]-benzylidene}-2,4-thiazolidene dione (13, X=OH)

The procedure described in example 30 was repeated except that 1.2 g (0.0099 mol) benzoic acid was used instead of acetic acid, and substantially the same results were achieved. In this particular case, the crude final product 5-{4-[2-(5-ethyl-pyridin-2-yl)-2-hydroxy-ethoxy]-benzylidene}-2,4-thiazolidene dione obtained was purified as described earlier to get 11 g (81%) pure product, which is identical in every respect with the product of example 30. m.p. 159° C.

EXAMPLE 34

5-{4-[2-(5-Ethyl-pyridin-2-yl)-2-hydroxy-ethoxy]-benzylidene}-2,4-thiazolidene dione (13, X=OH)

Into 132 mL methanol, 10 g (0.0369 mol) 4-[2-(5-ethyl-pyridin-2-yl)-2-hydroxy-ethoxy]-benzaldehyde, 4.74 g (0.0409 mol) thiazolidin-2,4-dione, 3.01 mL (0.0369 mol) pyrrolidine were added. Reaction mixture was warmed at 40-45° C. for 1 hr. and 3 mL (0.0525 mol) acetic acid was added. After completion of reaction on TLC, methanol was concentrated under reduced pressure and desired product was obtained as yellow powdered product. Yield of the product was 12.28 g (90%). m.p. 160° C.

The product obtained was characterized by IR, Mass, $^{13}C$ NMR, and $^1H$ NMR, which was found to be identical with the product obtained in example 30.

EXAMPLE 35

5-{4-[2-(5-Ethyl-pyridin-2-yl)-2-hydroxy-ethoxy]-benzylidene}-2,4-thiazolidene dione (13, X=OH)

94.98 g (0.811 mol) Thiazolidin-2,4-dione was added in 800 mL methanol followed by the addition of 200 g (0.738 mol) 4-[2-(5-ethyl-pyridin-2-yl)-2-hydroxy-ethoxy]-benzaldehyde and 60.92 mL (0.738 mol) pyrrolidine. Reaction mixture was warmed at 50-55° C. for 2 hr. and 48.26 mL (0.811 mol) acetic acid was added. Reaction mixture was stirred at 30° C. for 1 hr. Product precipitated was filtered off and purified using methanol to obtain yellow powdered desired product. Yield of the product was 248.48 g (91%). m.p. 160° C.

The product obtained was characterized by IR, Mass, $^{13}C$ NMR, and $^1H$ NMR, which as found to be identical with the product obtained in example 30.

EXAMPLE 36

5-{4-[2-(5-Ethyl-pyridin-2-yl)-2-hydroxy-ethoxy]-benzylidene}-2,4-thiazolidene dione (13, X=OH)

Into 40 lit. methanol, 4.749 Kg (40.55 mol) thiazolidin-2,4-dione, 10 Kg (36.9 mol) 4-[2-(5-ethyl-pyridin-2-yl)-2-hydroxy-ethoxy]-benzaldehyde and 30.46 lit. (36.9 mol) pyrrolidine were added. Reaction mixture was warmed at 50-55° C. for 2 hr. and was added 24.13 lit. (40.55 mol) acetic acid. Reaction mixture was stirred at 30° C. for 1 hr. Product precipitated was filtered off and purified using methanol to obtain 12.424 Kg (91%) of the desired product. m.p. 160° C.

The product obtained was characterized by IR, Mass, $^{13}$C NMR, and $^1$H NMR, which was found to be identical with the product obtained in example 30.

EXAMPLE 37

5-{4-[2-(5-Ethyl-pyridin-2-yl)-2-hydroxy-ethoxy]-benzyl}-2,4-thiazolidene dione (14, X=OH)

To a stirred mixture of 49 mL water and 84 mL dimethyl formamide (DIVER 7 g (0.01891 mol) 5-{4-[2-(5-ethyl-pyridin-2-yl)-2-hydroxy-ethoxy]-benzylidene}-2,4-thiazolidene dione, 1.91 (0.0164 mol) g dimethyl glyoxime (DMG) and 0.21 (0.0009 mol) g cobaltus chloride hexahydrate (CoCl$_2$.6H$_2$O) dissolved in 14 mL DMF were added at 60-65° C. To that 3.9 g sodium borohydride in 21 mL water was added slowly. Reaction mixture was stirred at 60-65° C. for 3 hrs. Reaction mixture was poured into excess of water and was extracted with ethyl acetate. Upon concentrating ethyl acetate, white product obtained. Yield of the product was 6.47 g (92%).

The product obtained was characterized by IR, Mass, $^{13}$C NMR, and $^1$H NMR, which are as given below.

IR spectrum (cm$^{-1}$): 3523 (O—H str.), 1703, 1739 (C=O str.), 1037 (C—O—C str.)

Mass spectrum (m/z): 373 (M+H)$^+$ $^{13}$C-NMR (DMSO-d$_5$): δ 176.0, 171.0, 158.39, 158.69, 147.9, 137.55, 135.8, 130.30, 128.68, 120.5, 115.38, 72.24, 71.97, 51.0, 35.1, 25.02, 15.39

$^1$H-NMR (DMSO-d$_6$): δ 11.96 (1H, s), 6.84-8.37 (7H, m), 5.74 (1H, s), 4.91 (1H, dd), 4.82 (1H, dd), 4.0 (1H, dd), 4.2 (1H, dd), 3.25 (1H, dd), 3.04 (1H, dd), 2.55 (2H, q), 1.19 (3H, t)

Melting point: 119-121° C.

The final product was dissolved into substantial amount of isopropyl alcohol and HCl gas was bubbled into it to get its corresponding hydrochloride salt which was characterized by IR, Mass, $^{13}$C NMR, and $^1$H NMR, which are as given below.

IR spectrum (cm$^{-1}$): 3246 (O—H str.), 1685, 1743 (C=O str.), 1056 (C—O—C str.)

Mass spectrum (m/z): 373.1 (M+H)$^+$ $^{13}$C-NMR (CD$_3$OD): δ 175.66, 171.63, 157.13, 153.8, 145.03, 142.03, 140.2, 130.37, 114.5, 70.82, 68.1, 52.93, 36.2, 24.65, 14.61

$^1$H-NMR (CD$_3$OD): δ 6.83-8.65 (7H, m), 5.45 (1H, t), 4.65 (1H, dd), 4.33 (2H, m), 3.30 (1H, dd), 3.05 (1H, dd), 2.86 (2H, q), 1.33 (3H, t)

Melting point: 146-148° C.

EXAMPLE 38

5-{4-[2-(5-Ethyl-pyridin-2-yl)-2-hydroxy-ethoxy]-benzyl}-2,4-thiazolidene dione (14, X=OH)

30 g (0.0794 mol) 5-{4-[2-(5-ethyl-pyridin-2-yl)-2-hydroxy-ethoxy]-benzylidene}-2,4-thiazolidene dione was dissolved in 210 mL water. To this was added a mixture of 6.42 (0.0553 mol) g DMG and 2.62 g (0.011 mol) CoCl$_2$.6H$_2$O dissolved in 60 mL DMF at 65-70° C., followed by slow addition of 12.33 (0.3332 mol) g sodium borohydride dissolved in 90 mL cold water at 70-85° C. After complete addition of sodium borohydride, reaction mixture was stirred at 65-70° C. for 4 hr. To reaction mixture excess water was added and product was extracted with chloroform. Organic layer was separated, dried (calcium chloride) and concentrated under reduced pressure to afford 28.35 g (94%) white product. m.p. 119° C.

The product obtained was characterized by IR, Mass, $^{13}$C NMR, and $^1$H NMR, which was found to be identical with the product obtained in example 37.

EXAMPLE 39

5-{4-[2-(5-Ethyl-pyridin-2-yl)-2-hydroxy-ethoxy]-benzyl}-2,4-thiazolidene dione (14, X=OH)

Into 115 mL of water, 10 g (0.0256 mol) 5-{4-[2-(5-ethyl-pyridin-2-yl)-2-hydroxy-ethoxy]-benzylidene}-2,4-thiazolidene dione, 0.62 g (0.0053 mol) DMG and 0.038 g (0.0001 mol) COCl$_2$.6H$_2$O dissolved in 20 mL DMF were added at 65-70° C. To this 4.56 g (0.1232 mol) sodium borohydride in 35 mL cold water was added slowly at 70-75° C. After complete addition of sodium borohydride, reaction mixture was stirred at 65-70° C. for 4 hr. and poured into excess of water. Product was extracted with chloroform. Layers were separated, organic layer was dried and concentrated under reduced pressure to obtain white product. The product was recrystallized by a mixture of 0.5 v/wt ethanol and 15 v/wt diisopropyl ether. Yield of the product was 9.45 g (94%). m.p. 119° C.

The product obtained was characterized by IR, Mass, $^{13}$C NMR, and $^1$H NMR, which was found to be identical with the product obtained in example 37.

EXAMPLE 40

5-{4-[2-(5-Ethyl-pyridin-2-yl)-2-hydroxy-ethoxy]-benzyl}-2,4-thiazolidene dione (14, X=OH)

To a flask fitted with an overhead stirrer, a thermometer and a condensor was added a solution of 100 g (0.256 mol) 5-{4-[2-(5-ethyl-pyridin-2-yl)-2-hydroxy-ethoxy]-benzylidene}-2,4-thiazolidene dione dissolved in 700 mL water at 65-70° C. To this was added 15.59 g (0.1344 mol) DMG and 6.42 g (0.0269 mol) CoCl$_2$.6H$_2$O dissolved in 200 mL DMF followed by slow addition of 30.67 g (0.8289 mol) sodium borohydride in 300 mL chilled water at 70-85° C. After complete addition of sodium borohydride, reaction mixture was stirred at 65-70° C. for 4 hr. and poured into excess of water. Subsequent work-up by extraction with methyl tert-butyl ether and concentrating organic solvent under reduced pressure afforded 95.51 g (95%) white product. m.p. 121° C.

The product obtained was characterized by IR, Mass, $^{13}$C NMR, and $^1$H NMR, which was found to be identical with the product obtained in example 37.

EXAMPLE 41

5-{4-[2-(5-Ethyl-pyridin-2-yl)-2-hydroxy-ethoxy]-benzyl}-2,4-thiazolidene dione (14, X=OH)

To a solution of 10 Kg (25.6 mol) 5-{4-[2-(5-ethyl-pyridin-2-yl)-2-hydroxy-ethoxy]-benzylidene}-2,4-thiazolidene dione dissolved in 70 lit. water at 65-70° C. was added 1.559 Kg (13.44 mol) DMG and 0.642 Kg (2.69 mol) CoCl$_2$.6H$_2$O dissolved in 20 lit. DMF followed by slow addition of 3.067 Kg (82.89 mol) sodium borohydride in 30 lit. water at 70-85° C. After complete addition of sodium borohydride, reaction mixture was stirred at 65-70° C. for 4 hr. and excess of water was added to the reaction mixture. Subsequent work-up with chloroform and concentrating organic solvent under reduced pressure afforded 9.551 Kg (95%) white product. m.p. 120° C.

The product obtained was characterized by IR, Mass, $^{13}$C NMR, and $^1$H NMR, which was found to be identical with the product obtained in example 37.

EXAMPLE 42

5-{4-[2-Chloro-2-(5-ethyl-pyridin-2-yl)-ethoxy]-benzyl}-2,4-thiazolidene dione and HCl salt (14, X=Cl)

To 2 g (0.0053 mol) of 5-{4-[2-(5-ethyl-pyridin-2-yl)-2-hydroxy-ethoxy]-benzyl}-2,4-thiazolidene dione dissolved in chloroform was added 1.34 g (0.0064 mol) PCl$_5$ at 25-30° C. and reaction mixture was stirred for 3 hr. at 25-30° C. Reaction mixture was poured in excess of water and made basic with 10% Na$_2$CO$_3$ solution. Product was extracted with chloroform and on removing solvent, 1.26 g (60%) of the desired product was obtained.

The product obtained was characterized by IR, Mass, $^{13}$C NMR, and $^1$H NMR, which are as given below.

IR spectrum (cm$^{-1}$): 3400 (N—H str.), 1683, 1747 (C=O str.), 1051 (C—O—C str.)

Mass spectrum (m/z): 391.2 (M+H)$^+$ $^{13}$C-NMR (DMSO-d$_6$): δ 175.7, 171.7, 156.7, 150.9, 145.0, 141.7, 141.5, 130.5, 129.5, 124.5, 114.6, 69.5, 96.8, 52.9, 36.2, 24.9, 14.8

$^1$H-NMR (DMSO-d$_6$): δ 12.0 (1H, s), 6.88-8.65 (7H, m), 5.74 (1H, t), 4.86 (1H, dd), 4.66 (2H, m), 3.30 (1H, dd), 3.05 (1H, dd), 2.71 (2H, q), 1.17 (3H, t)

The final product was dissolved into substantial amount of tert-butyl ether and HCl gas was bubbled into it to yield its corresponding hydrochloride salt which characterized by IR, Mass, $^{13}$C NMR and $^1$H NMR, which are as given below.

IR spectrum (cm$^{-1}$): 3369 (N—H str.), 1697, 1747 (C=O str.), 1055 (C—O—C str.), 715 (C—O—C str.)

Mass spectrum (m/z): 391.2 (M+H)$^+$ $^{13}$C-NMR (DMSO-d$_6$): δ 175.7, 171.7, 156.7, 150.3, 142.6, 129.5, 144.2, 142.2, 124.9, 130.5, 114.7, 69.4, 56.2, 52.9, 39.4, 36.2, 24.9, 14.7

$^1$H-NMR (DMSO-d$_6$): δ 13.12 (1H, br s), 12.0 (1H, s), 6.91-8.7 (7H, m), 5.82 (1H, t), 4.86 (1H, dd), 4.65 (2H, m), 3.0 (2H, m), 2.7 (2H, q), 1.19 (3H, t)

Melting point: 175-178° C.

EXAMPLE 43

5-{4-[2-Chloro-2-(5-ethyl-pyridin-2-yl)-ethoxy]-benzyl}-2,4-thiazolidene dione (14, X=Cl)

A mixture of 1 g (0.0026 mol) of 5-{4-[2-(5-ethyl-pyridin-2-yl)-2-hydroxy-ethoxy]-benzyl}-2,4-thiazolidene dione and 1.072 g (0.01 mol) CaCO$_3$ was added in 10 mL chloroform and cooled to 0° C. To this was added 0.671 (0.0032 mol) g PCl$_5$ in 3 min. Reaction mixture was stirred for 3 hr. After subsequent work-up in alkaline water, extracting product with chloroform and on concentrating 0.6 g (58%) of the desired dark liquid was obtained.

The product obtained was characterized by IR, Mass, $^{13}$C NMR, and $^1$H NMR, which was found to be identical with the product obtained in example 42.

EXAMPLE 44

5-{4-[2-Chloro-2-(5-ethyl-pyridin-2-yl)-ethoxy]-benzyl}-2,4-thiazolidene dione (14, X=Cl)

The procedure described in example 42 was repeated on 10 g scale except that dichloromethane was used as solvent, and substantially the same results were achieved. In this particular case, the final 5-{4-[2-chloro-2-(5-ethyl-pyridin-2-yl)-ethoxy]-benzyl}-2,4-thiazolidene dione obtained was 5.98 g (57%), is identical in every respect with the product of example 42.

EXAMPLE 45

5-{4-[2-Chloro-2-(5-ethyl-pyridin-2-yl)-ethoxy]-benzyl}-2,4-thiazolidene dione (14, X=Cl)

15 g (0.0403 mol) of 5-{4-[2-(5-ethyl-pyridin-2-yl)-2-hydroxy-ethoxy]-benzyl}-2,4-thiazolidene dione was suspended in 75 mL toluene. To this was added 12.56 g (0.0483 mol) PCl$_5$ at 60° C. in 15 min. Heating was continued for 3 hr. Reaction mixture was poured in excess of water and made alkaline with 10% Na$_2$CO$_3$ solution. The product was extracted with chloroform and on concentrating dried organic layer in vacuo furnished 8.97 g (57%) of the titled product.

The product obtained was characterized by IR, Mass, $^{13}$C NMR, and $^1$H NMR, which was found to be identical with the product obtained in example 42.

EXAMPLE 46

5-{4-[2-Chloro-2-(5-ethyl-pyridin-2-yl)-ethoxy]-benzyl}-2,4-thiazolidene dione hydrochloride (14, X=Cl)

To a solution of 2 g (0.00537 mol) of 5-{4-[2-(5-ethyl-pyridin-2-yl)-2-hydroxy-ethoxy]-benzyl}-2,4-thiazolidene dione dissolved in 30 mL dichloromethane was added 1.06 g (0.0134 mol) pyridine and cooled to −15° C. To this was added 1.2 g (0.0059 mol) PCl$_5$ in 10 min, at −15 to −20° C. The reaction mixture was stirred for 2 hr, at −15 to −20° C., 1 hr. at −5 to 0° C., and 2 hr. at 20 to 25° C. Subsequent work-up and salt formation as described earlier yielded 1.17 g (56%) of the desired product.

The product obtained was characterized by IR, Mass, $^{13}$C NMR, and $^1$H NMR, which was found to be identical with the product obtained in example 42.

EXAMPLE 47

5-{4-[2-Chloro-2-(5-ethyl-pyridin-2-yl)-ethoxy]-benzyl}-2,4-thiazolidene dione hydrochloride (14, X=Cl)

The procedure described in example 46 was repeated on same scale except that PCl$_5$ was taken 1.45 g (0.00697 mol) used, and substantially the same results were achieved. In this particular case, the final 5-{4-[2-chloro-2-(5-ethyl-pyridin-2-yl)-ethoxy]-benzyl}-2,4-thiazolidene dione hydrochloride obtained was 1.15 g (55%), is identical in every respect with the product of example 42.

EXAMPLE 48

5-{4-[2-Chloro-2-(5-ethyl-pyridin-2-yl)-ethoxy]-benzyl}-2,4-thiazolidene dione hydrochloride (14, X=Cl)

The procedure described in example 46 was repeated on same scale except that PCl$_5$ was taken 1.12 g (0.00537 mol) used, and substantially the same results were achieved. In this particular case, the final 5-{4-[2-chloro-2-(5-ethyl-pyridin-2-yl)-ethoxy]-benzyl}-2,4-thiazolidene dione hydrochloride obtained was 1.19 g (57%), is identical in every respect with the product of example 42.

EXAMPLE 49

5-{4-[2-Chloro-2-(5-ethyl-pyridin-2-yl)-ethoxy]-benzyl}-2,4-thiazolidene dione (14, X=Cl)

The procedure described in example 42 was repeated on same scale except that after completion of the reaction, it was quenched with triethylamine instead of water, and substantially the same results were achieved. In this particular case, the final product 5-{4-[2-chloro-2-(5-ethyl-pyridin-2-yl)-ethoxy]-benzyl}-2,4-thiazolidene dione and its salt obtained was 1.3 g (62%), is identical in every respect with the product of example 42. m.p. 177° C.

EXAMPLE 50

5-{4-[2-Chloro-2-(5-ethyl-pyridin-2-yl)-ethoxy]-benzyl}-2,4-thiazolidene dione (14, X=Cl)

To a solution of 25 g (0.067 mol) of 5-{4-[2-(5-ethyl-pyridin-2-yl)-2-hydroxy-ethoxy]-benzyl}-2,4-thiazolidene dione dissolved in 250 mL chloroform was added 12 g (0.10008 mol) thionyl chloride at reflux temperature in one hour. Reflux was continued for further one hour. Reaction mixture was cooled to 25° C. and added 100 mL water The mixture was washed with 10% Na$_2$CO$_3$ solution, organic layer was separated, dried and concentrated under reduced pressure to obtain 24.4 g (93%) of the titled product.

The product obtained was characterized by IR, Mass, $^{13}$C NMR, and $^1$H NMR, which was found to be identical with the product obtained in example 42.

EXAMPLE 51

5-{4-[2-Chloro-2-(5-ethyl-pyridin-2-yl)-ethoxy]-benzyl}-2,4-thiazolidene dione hydrochloride (14, X=Cl)

To a flask fitted with an overhead stirrer, a thermometer and a condenser was added a solution of 500 g (1.344 mol) of 5-{4-[2-(5-ethyl-pyridin-2-yl)-2-hydroxy-ethoxy]-benzyl}-2,4-thiazolidene dione dissolved in 3500 mL chloroform. To this was added 146.3 mL (2.01 mol) thionyl chloride dissolved in 500 mL chloroform at reflux temperature in one hour. Reaction mixture was refluxed for further two hours. The solvent was evaporated and ether was added. Precipitated HCl salt was filtered and dried to get the titled product. Yield of the product was 550.96 g (96%), m.p. 176-179° C.

The product obtained was characterized by IR, Mass, $^{13}$C NMR, and $^1$H NMR, which was found to be identical with the hydrochloride salt of the product obtained in example 42.

EXAMPLE 52

5-{4-[2-Chloro-2-(5-ethyl-pyridin-2-yl)-ethoxy]-benzyl}-2,4-thiazolidene dione hydrochloride (14, X=Cl)

The procedure described in example—51 was repeated on same scale except that thionyl chloride was taken 191.9 g (1.6128 mol) and reaction mixture was refluxed for 30 hr. after complete addition of thionyl chloride, the precipitated product was filtered off and dried. Substantially the same results were achieved. In this particular case, the final product 5-{4-[2-chloro-2-(5-ethyl-pyridin-2-yl)-ethoxy]-benzyl}-2,4-thiazolidene dione hydrochloride obtained was 522.27 g (91%), is identical in every respect with the HCl salt of example 49. m.p. 176-178° C.

EXAMPLE 53

5-{4-[2-Chloro-2-(5-ethyl-pyridin-2-yl)-ethoxy]-benzyl}-2,4-thiazolidene dione (14, X=Cl)

To 50 g (0.1344 mol) of 5-{4-[2-(5-ethyl-pyridin-2-yl)-2-hydroxy-ethoxy]-benzyl}-2,4-thiazolidene dione dissolved in 450 mL dichloromethane was added 19.5 mL (0.2679 mol) thionyl chloride dissolved in 50 mL chloroform at reflux temperature in one hour. Reflux was continued for two hours. Solvent was evaporated and ether added into it. Precipitated solid was filtered off and dried to get 55 g (96%) of the titled product.

The product obtained was characterized by IR, Mass, $^{13}$C NMR, and $^1$H NMR, which was found to be identical with the product obtained in example 42.

EXAMPLE 54

5-{4-[2-Chloro-2-(5-ethyl-pyridin-2-yl)-ethoxy]-benzyl}-2,4-thiazolidene dione hydrochloride (14, X=Cl)

To a stirred solution of 10 kg (26.88 mol) of 5-{4-[2-(5-ethyl-pyridin-2-yl)-2-hydroxy-ethoxy]-benzyl}-2,4-thiazolidene dione dissolved in 70 lit. chloroform was added 4.818 Kg (40.32 mol) thionyl chloride dissolved in chloroform at reflux temperature. Reaction mixture was refluxed further. After suitable workup HCl salt was precipitated. Precipitated solid was filtered and dried to get the titled product. Yield of the product was 10.9 kg (95%).

The product obtained was characterized by IR, Mass, $^{13}$C NMR, and $^1$H NMR, which was found to be identical with the hydrochloride salt of the product obtained in example 42.

EXAMPLE 55

5-{4-[2-(5-Ethyl-pyridin-2-yl)-ethoxy]-benzyl}-2,4-thiazolidene dione (1)

To 5 g (0.0121 mol) of 5-{4-[2-chloro-2-(5-ethyl-pyridin-2-yl)-ethoxy]-benzyl}-2,4-thiazolidene dione dissolved in 25 mL acetic acid was added 1.62 (0.0243 mol) g zinc in 5 min. Stirring continued for 15 hours at 25-30° C. Reaction mixture was poured in excess water, made alkaline using 10% Na$_2$CO$_3$ and extracted with ethyl acetate. After distilling off ethyl acetate in vacuo, methanol was added to precipitate out 1.13 g (25%) g of the crystalline solid product. The two impurities identified in this reaction were 5-ethyl-2-vinyl-pyridine 0.128 g (10%) and 5-(4-hydroxy benzyl)-thiazolidin-2,4-dione 0.342 g (12%).

The product obtained was characterized by IR, Mass, $^{13}$C NMR, and $^{1}$H NMR, which are as given below.

IR spectrum (cm$^{-1}$): 3417 (N—H str.), 1693, 1743 (C=O str.), 1037 (C—O—C str.)

Mass spectrum (m/z) 357.1 (M+H)$^{+}$ $^{13}$C-NMR (DMSO-d$_{6}$): δ 176.5, 172.5, 157.8, 152.1, 145.9, 142.0, 141.1, 131.2, 129.9, 127.8, 115.2, 66.2, 53.8, 37.0, 33.2, 25.4, 15.5

$^{1}$H-NMR (DMSO-d$_{6}$): δ 12.0 (1H, s), 6.84-8.71 (7H, m), 4.86 (1H, dd), 4.38 (2H, t), 3.48 (2H, t), 3.25 (1H, dd), 3.04 (1H, dd), 2.75 (2H, q), 1.21 (3H, t)

Melting point 172-175° C.

The final product was dissolved into 12 mL methanol and 0.05 mL con. HCl was added into it at 25° C. Reaction mixture was refluxed for 30 min. and cooled to 10° C. Precipitated hydrochloride salt was filtered off and dried to yield 1.1 g (22%) of the salt, which was characterized by IR, Mass, $^{13}$C NMR and $^{1}$H NMR, which are as given below.

IR spectrum (cm$^{-1}$): 3257 (N—H str.), 1689, 1743 (C=O str.), 1155, 1244 (C—O—C str.)

Mass spectrum (m/z): 357.1 (M+H)$^{+}$ $^{13}$C-NMR (DMSO-d$_{6}$): δ 175.7, 171.7, 157.0, 151.0, 141.1, 129.0, 145.4, 139.8, 127.2, 130.4, 114.4, 65.4, 53.0, 39.2, 36.2, 24.6, 14.6

$^{1}$H-NMR (DMSO-d$_{6}$): δ 12.09 (1H, s), 6.82-8.7 (7H, m), 4.8 (1H, dd), 4.38 (2H, t), 3.5 (2H, t), 3.0 (2H, m), 2.75 (2H, q), 1.21 (3H, t)

Melting point: 190-193° C.

EXAMPLE 56

5-{4-[2-(5-Ethyl-pyridin-2-yl)-ethoxy]-benzyl}-2,4-thiazolidene dione (1)

The procedure described in example 55 was repeated except that temperature was maintained 5-10° C., and substantially the same results were achieved. In this particular case, the final product 5-{4-[2-(5-ethyl-pyridin-2-yl)-ethoxy]-benzyl}-2,4-thiazolidene dione obtained was 0.911 g (20%), is identical in every respect with the product of example 55. m.p. 172° C.

EXAMPLE 57

5-{4-[2-(5-Ethyl-pyridin-2-yl)-ethoxy]-benzyl}-2,4-thiazolidene dione (1)

To a solution of 0.8 g (0.00184 mol) of 5-{4-[2-chloro-2-(5-ethyl-pyridin-2-yl)-ethoxy]-benzyl}-2,4-thiazolidene dione dissolved in 10 mL ethyl acetate was added 0.8 mL (0.014 mol) acetic acid and 0.119 g (0.00184 mol) zinc in 5 minutes at 25-30° C. Stirring continued for 9 hr. at 30-35° C. Solid material separated was filtered off and dried to get titled compound. Yield of the product was 0.3 g (41%). m.p. 173° C.

The product obtained was characterized by IR, Mass, $^{13}$C NMR, and $^{1}$H NMR, which was found to be identical with the product obtained in example 55. The impurity profile was also similar to the product obtained in example 55.

EXAMPLE 58

5-{4-[2-(5-Ethyl-pyridin-2-yl)-ethoxy]-benzyl}-2,4-thiazolidene dione (1)

The procedure described in example 57 was repeated except that acetic acid was replaced by 1.038 g (0.014 mol) propionic acid, and substantially the same results were achieved. In this particular case, the final product 5-{4-[2-(5-ethyl-pyridin-2-yl)-ethoxy]-benzyl}-2,4-thiazolidene dione obtained was 0.3 g (41%), is identical in every respect with the product of example 55. m.p. 172° C.

EXAMPLE 59

5-{4-[2-(5-Ethyl-pyridin-2-yl)-ethoxy]-benzyl}-2,4-thiazolidene dione (1)

The procedure described in example 57 was repeated except that tetrahydrofuran was used as solvent, and substantially the same results were achieved. In this particular case, the final product 5-{4-[2-(5-ethyl-pyridin-2-yl)-ethoxy]-benzyl}-2,4-thiazolidene dione obtained was 0.13 g (18%), is identical in every respect with the product of example 55. m.p. 173° C.

EXAMPLE 60

5-{4-[2-(5-Ethyl-pyridin-2-yl)-ethoxy]-benzyl}-2,4-thiazolidene dione (1)

To a mixture of 5 mL 35% Con. HCl and 5 mL water, 0.5 g (0.0012 mol) of 5-{4-[2-chloro-2-(5-ethyl-pyridin-2-yl)-ethoxy]-benzyl}-2,4-thiazolidene dione was added followed by the addition of 0.039 g (0.0006 mol) zinc (tlc). Reaction mixture was poured into 20 mL water, made alkaline by 10% K$_{2}$CO$_{3}$ solution and product was extracted with 25 mL ethyl acetate. Organic layer was separated, dried (magnesium sulfate) and concentrated under reduced pressure. Methanol was added to the residual mass to get 0.1 g (22%) crystalline titled product. m.p. 174° C.

The product obtained was characterized by IR, Mass, $^{13}$C NMR, and $^{1}$H NMR, which was found to be identical with the product obtained in example 55.

EXAMPLE 61

5-{4-[2-(5-Ethyl-pyridin-2-yl)-ethoxy]-benzyl}-2,4-thiazolidene dione (1)

To a mixture of 35 mL ethanol and 7 mL (0.122 mol) glacial acetic acid was dissolved 3.5 g (0.0084 mol) of 5-{4-[2-chloro-2-(5-ethyl-pyridin-2-yl)-ethoxy]-benzyl}-2,4-thiazolidene dione followed by addition of 0.819 g (0.0126 mol) zinc. Precipitated product was filtered and dried to yield 1.91 g (60%) product. m.p. 174° C.

The product obtained was characterized by IR, Mass, $^{13}$C NMR and $^{1}$H NMR, which was found to be identical with the product obtained in example 55.

EXAMPLE 62

5-{4-[2-(5-Ethyl-pyridin-2-yl)-ethoxy]-benzyl}-2,4-thiazolidene dione (1)

Into 10 mL (0.175 mol) glacial acetic acid, 1 g (0.0024 mol) of 5-{4-[2-chloro-2-(5-ethyl-pyridin-2-yl)-ethoxy]-benzyl}-2,4-thiazolidene dione and 100 mg (0.0018 mol) ammonium chloride were dissolved. Under stirring 0.078 g (0.0012 mol) zinc was added. Subsequent work-up in water yielded 0.6 g (66%) of the desired product. m.p. 175° C.

The product obtained was characterized by IR, Mass, $^{13}$C NMR, and $^{1}$H NMR, which was found to be identical with the product obtained in example 55.

EXAMPLE 63

5-{4-[2-(5-Ethyl-pyridin-2-yl)-ethoxy]-benzyl}-2,4-thiazolidene dione (1)

The procedure described in example 61 was repeated on 5 g scale except that isopropyl alcohol was used as solvent and reaction mixture was allowed to stir for 8 hours. Substantially the same results were achieved. In this particular case, the final product 5-{4-[2-(5-ethyl-pyridin-2-yl)-ethoxy]-benzyl}-2,4-thiazolidene dione obtained was 3 g (66%), is identical in every respect with the product of example 55. m.p. 174° C.

EXAMPLE 64

5-{4-[2-(5-Ethyl-pyridin-2-yl)-ethoxy]-benzyl}-2,4-thiazolidene dione (1)

0.63 g (0.0097 mol) Zinc dust and 8.93 mL (0.0582 mol) tetramethyl ethylenediamine were added into 80 mL ethanol under nitrogen atmosphere. To this a mixture of 1.18 mL acetic acid and 7.8 g (0.0194 mol)) of 5-{4-[2-chloro-2-(5-ethyl-pyridin-2-yl)-ethoxy]-benzyl}-2,4-thiazolidene dione dissolved in 16 mL ethanol was added in 15 min. at 5-10° C. Reaction mixture was allowed to achieve 27° C. and 4.74 mL acetic acid was added in 15 minutes. Reaction mixture was stirred for 15 hr. The product precipitated was filtered off and dried to obtain 3.98 g (56%) of the titled product. m.p. 173° C.

The product obtained was characterized by IR, Mass, $^{13}$C NMR, and $^1$H NMR, which was found to be identical with the product obtained in example 55.

EXAMPLE 65

5-{4-[2-(5-Ethyl-pyridin-2-yl)-ethoxy]-benzyl}-2,4-thiazolidene dione (1)

To a mixture of 40 mL ethanol and 10 mL propionic acid, 5 g (0.0117 mol) of 5-{4-[2-chloro-2-(5-ethyl-pyridin-2-yl)-ethoxy]-benzyl}-2,4-thiazolidene dione hydrochloride was dissolved. To this was added 1.5 g (0.0234 mol) of zinc and stirred. Reaction mixture was stirred for 12 hr. Product precipitated was filtered off and dried to yield 2 g (48%) of the titled product. m.p. 175° C.

The product obtained was characterized by IR, Mass, $^{13}$C NMR, and $^1$H NMR, which was found to be identical with the product obtained in example 55.

EXAMPLE 66

5-{4-[2-(5-Ethyl-pyridin-2-yl)-ethoxy]-benzyl}-2,4-thiazolidene dione (1)

70 g (0.150 mol) of 5-{4-[2-chloro-2-(5-ethyl-pyridin-2-yl)-ethoxyl]-benzyl}-2,4-thiazolidene dione dissolved in a mixture methanol and acetic acid. To this was added 21.85 g (0.3 mol) of and stirred. Product precipitated was filtered off and dried to get 51 g (80%) of the desired product. The impurity profile in this reaction was similar to the impurity profile described in example 55. m.p. 174° C.

The product obtained was characterized by IR, Mass, $^{13}$C NMR, and $^1$H NMR, which was found to be identical with the product obtained in example 55.

The final product obtained above was treated with conc. HCl in isopropanol. Precipitated hydrochloride salt was filtered off and dried to yield 50 g of the salt, which was characterized by IR, Mass, $^{13}$C NMR and $^1$H NMR, which was found identical with hydrochloride salt obtained in example 55. m.p. 194-197° C.

EXAMPLE 67

5-{4-[2-(5-Ethyl-pyridin-2-yl)-ethoxy]-benzyl}-2,4-thiazolidene dione (1)

A solution of 250 g (0.5854 mol) of 5-{4-[2-chloro-2-(5-ethylpyridin-2-yl)-ethoxy]-benzyl}-2,4-thiazolidene dione hydrochloride in methanol and 500 mL (8.75 mol) acetic acid was added into a flask fitted with an overhead stirrer and a thermometer. To this was added 76.54 g (1.17 mol) of and stirred. The product precipitated was filtered and dried. Yield of the product was 100 g (48%). The impurity profile in this reaction was similar to the impurity profile described in example 55. m.p. 175° C.

The product obtained was characterized by IR, Mass, $^{13}$C NMR, and $^1$H NMR, which was found to be identical with the product obtained in example 55.

The final product treated with conc. HCl in ethanol. Precipitated hydrochloride salt was filtered off and dried to yield 100 g of the salt, which was characterized by IR, Mass, $^{13}$C NMR and $^1$H NMR, which was found identical with hydrochloride salt obtained in example 55. m.p. 192° C.

EXAMPLE 68

5-{4-[2-(5-Ethyl-pyridin-2-yl)-ethoxy]-benzyl}-2,4-thiazolidene dione (1)

10 kg (23.42 mol) of 5-{4-[2-chloro-2-(5-ethyl-pyridin-2-yl)-ethoxy]-benzyl}-2,4-thiazolidene dione hydrochloride was dissolved in a mixture of 80 lit. methanol and 20 lit. acetic acid. To this was added 3.06 kg (46.8 mol) of zinc and stirred (tlc). Product precipitated was filtered off and dried to get 7.5 Kg of the desired product. m.p. 172° C.

The product obtained was converted into its hydrochloride salt as described in example 67 to obtain 7.72 Kg (84%) of the salt, which was found to be identical in all respect with the salt obtained in example 55. The impurity profile in this reaction was similar to the impurity profile described in example 55. m.p. 192° C.

EXAMPLE 69

5-{4-[2-(5-Ethyl-pyridin-2-yl)-2-mesyl-ethoxy]-benzylidene}-2,4-thiazolidene dione (13, X=OMs)

A mixture of 5 g (0.0135 mol) of 5-{4-[2-(5-ethyl-pyridin-2-yl)-2-hydroxy-ethoxy]-benzylidene}-2,4-thiazolidene dione and 1.63 g (0.0162 mol) triethyl amine was suspended in 50 mL dichloromethane and cooled to 0-5° C. To this was added 1.5 g (0.0135 mol) of mesyl chloride dissolved in 10 mL dichloromethane at 0-5° C. Reaction mixture was stirred for 2 hr. Subsequent work-up in excess water gave crude 3 g product, which was purified by column chromatography to get the titled product. Yield of the product was 4.54 g (75%).

The product obtained was characterized by IR, Mass and $^1$H NMR, which are as given below.

IR spectrum (cm$^{-1}$): 1739, 1701 (C=O str.), 1342 (S=O str.)

Mass spectrum (m/z): 449.1 (M+H)$^+$ $^1$H-NMR (DMSO-d$_6$): δ 12.3 (1H, s), 7.8 (1H, s), 6.95-7.74 (7H, m), 5.99 (1H, dd), 4.54 (2H, m), 3.1 (3H, s), 2.68 (2H, q), 1.27 (3H, t)

Melting point: 60-65° C.

EXAMPLE 70

5-{4-[2-(5-Ethyl-pyridin-2-yl)-2-mesyl-ethoxy]-benzyl}-2,4-thiazolidene dione (14, X=OMs)

To a suspension of 1 g (0.0022 mol) of 5-{4-[2-(5-ethyl-pyridin-2-yl)-2-mesyl-ethoxy]-benzylidene}-2,4-thiazolidene dione in 10 mL aq. methanol was added 0.5 g of 10% palladium charcoal. Reaction mixture was subjected to hydrogenation in Parr apparatus for 14 hr. at 60 psi. After subsequent work up 0.3 g crude product obtained, which was purified to get the desired product. Yield of the product was 0.22 g (22%).

The product obtained was characterized by Mass and $^1$H NMR, which are as given below.

Mass spectrum (m/z): 451.1 (M+H)$^+$
$^1$H-NMR (DMSO-d$_6$): δ 12.2 (1H, s), 6.8-8.4 (7H, m), 5.6 (1H, dd), 4.13 (1H, dd), 4.54 (2H, m), 3.4 (2H, m), 3.1 (3H, s), 2.68 (2H, q), 1.2 (3H, t)

EXAMPLE 71

5-{4-[2-(5-Ethyl-pyridin-2-yl)-ethoxy]-benzyl}-2,4-thiazolidene dione (1)

1 g (0.0022 mol) of 5-{4-[2-(5-ethyl-pyridin-2-yl)-2-mesyl-ethoxy]-benzyl}-2,4-thiazolidene dione was added into 10 mL acetic acid. To this was added 0.246 gm (0.0066 mol) sodium borohydride at 40-45° C. in 5 min. Reaction mixture was stirred for 15 hr. at 40-45° C. After subsequent work up crude product was obtained which yielded the titled product after purification. Yield of the product was 0.079 g (10%).

The product obtained was characterized by IR, Mass, $^{13}$C NMR, and $^1$H NMR, which was found to be identical with the product obtained in example 55.

EXAMPLE 72

5-{4-[2-(5-Ethyl-pyridin-2-yl)-2-mesyl-ethoxy]-benzyl}-2,4-thiazolidene dione (14, X=OMs)

1.63 g (0.0161 mol) triethyl amine was added to a mixture of 5 g (0.0134 mol) of 5-{4-[2-(5-ethyl-pyridin-2-yl)-2-hydroxy-ethoxy]-benzyl}-2,4-thiazolidene dione and 1.538 g (0.0134 mol) of mesyl chloride in 60 mL dichloromethane at 0° C. Reaction mixture was stirred for 2 hr. The progress of reaction was monitored on TLC and after completion of reaction, subsequent work-up in excess water and purification of the crude product yielded 4.23 g (70%) of the desired product.

The product obtained was characterized by IR, Mass, $^{13}$C NMR and $^1$H NMR, which was found to be identical with the product obtained in example 70.

EXAMPLE 73

5-{4-[2-(5-Ethyl-pyridin-2-yl)-ethoxy]-benzyl}-2,4-thiazolidene dione (1)

To 1 g (0.0022 mol) of 5-{4-[2-(5-ethyl-pyridin-2-yl)-2-mesyl-ethoxy]-benzylidene}-2,4-thiazolidene dione suspended in 7 mL water was added a dissolved mixture of 0.13 g (0.0011 mol) dimethylglyoxime and 0.053 g (0.00022 mol) cobaltous chloride hexahydrate in 2 mL DMF at 65-70° C. To this 0.34 g (0.0092 mol) of sodium borohydride dissolved in 5 mL of water was added drop wise. Reaction mixture was stirred at 60-65° C. for 3 hrs. Subsequent work-up which involved addition of water, extraction of the product with ethyl acetate, concentrating ethyl acetate in vacuo yielded white desired product. Yield of the product was 0.119 g (15%).

The product obtained was characterized by IR, Mass, $^{13}$C NMR, and $^1$H NMR, which was found to be identical with the product obtained in example 55.

EXAMPLE 74

5-{4-[2-(5-Ethyl-pyridin-2-yl)-2-tosyl-ethoxy]-benzylidene}-2,4-thiazolidene dione (13, X=OTs)

1.63 g (0.0161 mol) triethylamine was added to a stirred solution of 5 g (0.0135 mol) of 5-{4-[2-(5-ethyl-pyridin-2-yl)-2-hydroxy-ethoxy]-benzylidene}-2,4-thiazolidene dione and 2.57 g (0.0135 mol) of tosyl chloride dichloromethane was added and cooled at 0° C. Reaction mixture was stirred for 2 hr. Progress of the reaction was monitored by TLC and after completion of the reaction, subsequent work-up in excess water gave crude product, which was purified to obtain the titled product. Yield of the product was 5.66 g (80%).

The product obtained was characterized by Mass and $^1$H NMR, which are as given below.

Mass spectrum (m/z): 525 (M+H)$^+$
$^1$H-NMR (DMSO-d$_6$): δ 12.4 (1H, s), 7.1 (1H, s), 6.85-8.48 (11H, m), 5.5 (1H, dd), 4.5 (2H, m), 2.68 (2H, q), 2.38 (3H, s), 1.2 (3H, t)

EXAMPLE 75

5-{4-[2-(5-Ethyl-pyridin-2-yl)-2-tosyl-ethoxy]-benzyl}-2,4-thiazolidene dione (14, X=OTs)

To 1 g (0.0019 mol) of 5-{4-[2-(5-ethyl-pyridin-2-yl-)-2-tosyl-ethoxy]-benzylidene}-2,4-thiazolidene dione suspended in 10 mL aq. methanol was added 0.5 g of 10% palladium charcoal. Reaction mixture was subjected to hydrogenation in Parr apparatus for 14 hr. at 60 psi. After subsequent work up and purification led to 0.2 g (20%) of the desired product. Further reduction of product to 1 was also observed 0.135 g (20%).

The product obtained was characterized by Mass and $^1$H NMR, which are as given below.

Mass spectrum (m/z): 527.1 (M+H)$^+$
$^1$H-NMR (DMSO-d$_6$): δ 12.3 (1H, s), 6.8-8.4 (11H, m), 5.65 (1H, dd), 4.6 (1H, dd), 4.4 (2H, m), 3.34 (2H, m), 2.64 (2H, q), 2.4 (3H, s), 1.19 (3H, t)

EXAMPLE 76

5-{4-[2-(5-Ethyl-pyridin-2-yl)-ethoxy]-benzyl}-2,4-thiazolidene dione (1)

Into 10 mL acetic acid, 1.167 g (0.0022 mol) of 5-{4-[2-(5-ethyl-pyridin-2-yl)-2-tosyl-ethoxy]-benzyl}-2,4-thiazolidene dione and 0.246 g (0.0066 mol) sodium borohydride were added at 40-45° C., Reaction mixture was stirred for 15 hr. at 40-45° C. After subsequent work up crude product was obtained which yielded the titled product after purification. Yield of the product was 0.039 g (5%).

The product obtained was characterized by IR, Mass, $^{13}$C NMR, and $^1$H NMR, which was found to be identical with the product obtained in example 55.

EXAMPLE 77

5-{4-[2-(5-Ethyl-pyridin-2-yl)-2-tosyl-ethoxy]-benzyl}-2,4-thiazolidene dione (14, X=OTs)

1.56 g (0.0154 mol) triethylamine was added to a solution of 5 g (0.0134 mol) of 5-{4-[2-(5-ethyl-pyridin-2-yl-)-2-hydroxy-ethoxy]-benzyl}-2,4-thiazolidene dione and 2.55 g (0.0134 mol) of tosyl chloride dichloromethane at 0° C. Reaction mixture was stirred for 2 hr. Progress of the reaction was monitored by TLC and after completion of the reaction, subsequent work-up in excess water and purification of the crude product yielded 5.30 g (75%) of the desired product.

The product obtained was characterized by IR, Mass, $^{13}C$ NMR and $^1H$ NMR, which was found to be identical with the product obtained in example 75.

EXAMPLE 78

5-{4-[2-(5-Ethyl-pyridin-2-yl)-ethoxy]-benzyl}-2,4-thiazolidene dione (1)

To 1 g (0.0019 mol) of 5-{4-[2-(5-ethyl-pyridin-2-yl-)-2-tosyl-ethoxy]-benzylidene}-2,4-thiazolidene dione suspended in 7 mL water was added a dissolved mixture of 0.11 g (0.001 mol) dimethylglyoxime and 0.045 g (0.00018 mol) cobaltus chloride hexahydrate in 2 mL DMF at 65-70° C. To this 0.29 g (0.0078 mol) of sodium borohydride in 5 mL of water was added drop wise. Reaction mixture was stirred at 60-65° C. for 3 hr. Progress of the reaction was monitored by TLC and after completion of reaction, the work-up involved addition of excess of water, extraction of the product with ethyl acetate, removal of the organic solvent in vacuo which yielded 0.04 g (6%) of the crystalline product.

The product obtained was characterized by IR, Mass, $^{13}C$ NMR, and $^1H$ NMR, which was found to be identical with the product obtained in example 55.

EXAMPLE 79

5-{4-[2-Chloro-2-(5-ethyl-pyridn-2-yl)-ethoxy]-benzylidene}-2,4-thiazolidene dione (13, X=Cl)

To a stirred solution of 5 g (0.0135 mol) of 5-{4-[2-(5-ethyl-pyridin-2-yl)-2-hydroxy-ethoxy]-benzylidene}-2,4-thiazolidene dione dissolved in 40 mL chloroform was added 1.47 ml (0.02 mol) thionyl chloride dissolved in 2 mL chloroform at reflux temperature in one hour. Reflux was continued for further two hour. Chloroform was distilled out ether was added into it. Precipitated solid was filtered off and dried to obtain 4.5 g (86%) of the desired product.

The product obtained was characterized by IR, Mass, $^{13}C$ NMR, and $^1H$ NMR, which are as given below.

IR spectrum (cm$^{-1}$): 3409 (N—H str.), 1689, 1735 (C=O str.), 1043 (C—O—C str.)

Mass spectrum (m/z): 389 (M+H)$^+$ $^{13}C$-NMR (DMSO-d$_6$): δ 167.9, 167.4, 159.2, 150.2, 144.3, 142.5, 142.2, 132.1, 131.6, 126.3, 124.9, 120.8, 115.6, 69.5, 56.1, 25.0, 14.8

$^1H$-NMR (DMSO-d$_6$): δ 11.18 (1H, s), 7.08-8.69 (7H, m), 7.6 (1H, s), 5.85 (1H, t), 4.76 (2H, d), 2.71 (2H, q), 1.15 (3H, t)

Melting point: 177-181° C.

EXAMPLE 80

5-{4-[2-Chloro-2-(5-ethyl-pyridn-2-yl)-ethoxy]-benzyl}-2,4-thiazolidene dione (14, X=Cl)

To a stirred solution of 1 g (0.0026 mol) of 5-{4-[2-chloro-2-(5-ethyl-2-pyridyl)-ethoxy]-benzylidene}-2,4-thiazolidene dione dissolved in 10 mL aq. methanol was added 0.5 g 10% Pd/C. Reaction mixture was subjected to hydrogenation in Parr apparatus for 16 hr. at 60 psi pressure. After subsequent work-up and purification furnished titled product. Yield of the product was 0.29 g (29%). Further reduction of product to 1 was also observed 0.09 g (10%).

The product obtained was characterized by IR, Mass, $^{13}C$ NMR and $^1H$ NMR, which was found to be identical with the product obtained in example 42 and example 55.

EXAMPLE 81

5-{4-[2-Chloro-2-(5-ethyl-pyridn-2-yl)-ethoxy]-benzyl}-2,4-thiazolidene dione (14, X=Cl)

To a stirred solution of 1 g (0.0026 mol) of 5-{4-[2-chloro-2-(5-ethyl-2-pyridyl)ethoxy]-benzylidene}-2,4-thiazolidene dione dissolved in 10 mL tetrahydrofuran was added 1 g Raney—Ni and H$_2$ gas was passed through reaction mixture for 12 hr. After subsequent work-up and purification titled product was obtained. Yield of the product was 0.40 g (40%). Further reduction of product to 1 was also observed. 0.073 g (8%).

The product obtained was characterized by IR, Mass, $^{13}C$ NMR and $^1H$ NMR, which was found to be identical with the product obtained in example 42 and example 55.

EXAMPLE 82

5-{4-[2-(5-Ethyl-pyridin-2-yl)-ethoxy]-benzyl}-2,4-thiazolidene dione (1)

In a mixture of 8 mL methanol and 2 mL (0.035 mol) acetic acid, 1 g (0.0025 mol) of 5-{4-[2-chloro-2-(5-ethyl-2-pyridyl)-ethoxy]-benzyl}-2,4-thiazolidene dione was dissolved. To this was added 0.33 g (0.005 mol) Zinc at 25-30° C. Reaction mixture was stirred for 15 hr., precipitated product was filtered and dried to get 0.3 g (33%) of the titled product.

The product obtained was characterized by IR, Mass, $^{13}C$ NMR, and $^1H$ NMR, which was found to be identical with the product obtained in example 55.

EXAMPLE 83

5-{4-[2-(5-Ethyl-pyridin-2-yl)-ethoxy]-benzyl}-2,4-thiazolidene dione (1)

A mixture of 0.15 g (0.0013 mol) dimethylglyoxime and 0.061 g (0.0002 mol) CoCl$_2$. 6H$_2$O in 2 mL of DMF was added to a suspension of 1 g (0.0026 mol) of 5-{4-[2-chloro-2-(5-ethyl-2-pyridyl)-ethoxy]-benzylidene}-2,4-thiazolidene dione in 7 mL of water at 65-70° C. followed by drop wise addition of 0.399 g (0.0107 mol) sodium borohydride. After complete addition of sodium borohydride reaction mixture was stirred at 65-70° C. for 4 hrs. Product was extracted with methyl tert-butyl ether. After concentrating solvent up to 90%, 20 mL cyclohexane was added to the reaction mixture with stirring. The product precipitated was filtered off and dried. Yield of the product was 0.054 g (6%).

The product obtained was characterized by IR, Mass, $^{13}$C NMR, and $^1$H NMR, which was found to be identical with the product obtained in example 55.

EXAMPLE 84

5-{4-[2-(5-Ethyl-pyridn-2-yl)-ethoxy]-benzylidene}-2,4-thiazolidene dione (13, X=H)

In a mixture of 8 mL methanol and 2 mL (0.035 mol) acetic acid, 1 g (0.0025 mol) of 5-{4-[2-chloro-2-(5-ethyl-2-pyridyl)-ethoxy]-benzylidene}-2,4-thiazolidene dione was dissolved. To this was added 0.33 g (0.005 mol) Zinc at 25-30° C. Reaction mixture was stirred for 15 hr., precipitated product was filtered off and dried to yield 0.55 g (60%) of the titled product.

The product obtained was characterized by comparison with a reference sample prepared by a known method (see prior art).

EXAMPLE 85

5-{4-[2-(5-Ethyl-pyridin-2-yl)-ethoxy]-benzyl}-2,4-thiazolidene dione (1)

To a solution of 1 g (0.0028 mol) of 5-{4-[2-(5-ethyl-2-pyridyl)-ethoxy]-benzylidene}-2,4-thiazolidene dione dissolved in 10 mL aq. methanol was added 0.5 g 10% Pd/C. Reaction mixture was subjected to hydrogenation in Parr apparatus for 16 hr. at 60 psi. Progress of the reaction was monitored by TLC and after completion of the reaction, subsequent work-up furnished the titled product. Yield of the product was 0.35 g (35%).

The product obtained was characterized by IR, Mass, $^{13}$C NMR and $^1$H NMR, which was found to be identical with the product obtained in example 55.

EXAMPLE 86

2-Bromo-[5-ethyl-pyridin-2-yl]-ethyl bromide (3, X=Br)

To a cooled solution (0-5° C.), of 3 g (0.0221 mol) of-5-ethyl-2-vinyl-pyridine dissolved in 50 mL carbon tetrachloride was added 1.13 mL (0.0221 mol) bromine in 10 mL CCl$_4$ drop wise. Reaction mixture was stirred for 2 hr. After concentrating CCl$_4$ under reduced pressure 2.84 g (43%) titled product was obtained.

The product obtained was characterized by Mass and $^1$H NMR, which are as given below.

Mass spectrum (m/z): 294 (M+H)$^+$ $^1$H-NMR (DMSO-d$_6$): δ 7.9-8.6 (3H, m), 5.9 (1H, dd), 4.20-4.45 (2H, m), 2.8 (2H, q), 1.3 (3H, t)

EXAMPLE 87

4-[2-Bromo-2-(5-ethyl-pyridn-2-yl)-ethoxy]-benzaldehyde (9, X=Br)

To a stirred solution of 0.67 g (0.0055 mol) p-hydroxy benzaldehyde and 0.237 g (0.0098 mol) sodium hydride in 10 mL DMF, 1 g (0.0034 mol) 2-bromo-[5-ethyl-2-pyridyl]-ethyl bromide dissolved in 10 mL of DMF was added at 10-15° C. Reaction mixture was stirred for 1 hr at 25-30° C. and further warmed at 75-80° C. for 24 hr. After subsequent work-up crude product was obtained which on purification gave titled compound. Yield of the product was 0.068 g (6%). The product obtained was characterized by satisfactory mass.

EXAMPLE 88

2-(5-Ethyl-1-oxy-pyridin-2-yl)-ethanol (16)

To a solution of 100 g (0.655 mol) 2-(5-ethyl-pyridin-2-yl)-ethanol in 500 mL acetic acid was added 118 g (1.049 mol) 30% hydrogen peroxide at 25-30° C. Reaction mixture was refluxed at 100° C. (tlc) for 14 hr. After completion of the reaction acetic acid was removed under vacuum, and the residual mass was poured in excess water and made alkaline by 10% Na$_2$CO$_3$ solution. Product was extracted with ethyl acetate and after concentrating ethyl acetate in vacuo, 89.58 g (81%) crystalline product was obtained.

The product obtained was characterized by Mass, $^{13}$C NMR, and $^1$H NMR, which are as given below.

Mass spectrum (m/z): 168.1 (M+H)$^+$ $^{13}$C-NMR (CDCl$_3$): δ 170.7, 148.2, 138.7, 135.9, 125.8, 62.0, 34.2, 25.5, 14.4

$^1$H NMR (CDCl$_3$): δ 707-8.14 (3H, m), 5.7 (1H, broad s), 3.9 (2H, t), 3.2 (2H, t), 2.6 (2H, q), 1.2 (3H, t)

EXAMPLE 89

Acetic acid 2-acetoxy-2-(5-ethyl-1-pyridin-2-yl)-ethyl ester (17)

14.6 g (0.14 mol) Acetic anhydride was added to 20 g (0.11 mol) of 2-(5-ethyl-1-oxy-pyridin-2-yl)-ethanol. Reaction mixture was heated at 120° C. for 30 min. Reaction mixture was quenched with water and product was extracted with ethyl acetate. Ethyl acetate was dried and concentrated under reduced pressure to get the crude product which after purification gave acetic acid 2-acetoxy-2-(5-ethyl-1-pyridin-2-yl) ethyl ester. Yield of the product was 7.81 g (26%).

The product obtained was characterized by IR, Mass, $^{13}$C NMR, and $^1$H NMR, which are as given below.

IR spectrum (cm$^{-1}$): 1741 (C=O str.); 1047 (C—O—C str.)

Mass spectrum (m/z): 252.1 (M+H)$^+$ $^{13}$C-NMR (DMSO-d$_6$): δ 170.3, 169.9, 152.9, 149.0, 138.8, 135.8, 121.2, 73.6, 64.9, 29.4, 25.5, 20.8, 14.9

$^1$H-NMR (DMSO-d$_6$): δ 7.28-8.44 (3H, m), 6.0 (1H, dd), 4.43-4.58 (2H, m), 2.6 (2H, q), 2.1 (3H, s), 2.0 (3H, s), 1.2 (3H, t)

EXAMPLE 90

1-(5-Ethyl-pyridin-2-yl)-ethan-1,2-diol (11)

19.91 g (0.497 mol) Sodium hydroxide was added to a solution of 71 g (0.226 mol) acetic acid 2-acetoxy-2-(5-ethyl-pyridin-2-yl)-ethyl ester in 355 mL water. Reaction mixture was stirred at 40° C. for 2 hr. After completion of reaction on TLC, reaction mixture was neutralized with con. HCl and precipitated solid was filtered off and dried to get 1-(5-ethyl-pyridin-2-yl)-ethan-1,2-diol. Yield of the product was 32.1 E (68%).

The product obtained was characterized by IR, Mass, $^{13}$C NMR, and $^1$H NMR, which are as given below.

IR spectrum (cm$^{-1}$): 3400-3500 (O—H str.), 2875-2972 (C—H str.)

mass spectrum (m/z): 168.1 (M+H)$^+$ $^{13}$C-NMR (CDCl$_3$): δ 170.1, 147.7, 138.4, 136.4, 120.5, 73.2, 67.1, 25.6, 15.2

$^1$H-NMR (CDCl$_3$): δ 7.27-8.34 (3H, m), 4.9 (1H, m), 4.82 (2H, broad s), 3.71-3.94 (2H, m), 2.65 (2H, q), 1.25 (3H, t)

EXAMPLE 91

5-Ethyl-2-[2-oxo-(1,3,2)-dioxathiolan-4-yl]-pyridine (10)

4.98 mL (0.0387 mol) triethylamine was added to a solution of 3 g (0.017 mol) 1-(5-ethyl-pyridin-2-yl)-ethan-1,2-diol dissolved in 60 mL dichloromethane at 0-5° C. To this 1.43 mL (0.019 mol) thionyl chloride was added drop wise in 15 min and stirring was continued for 1 hr. Reaction mixture was quenched with 10% sodium bicarbonate solution. Product was extracted with dichloromethane, which was concentrated in vacuo to obtain titled product. Yield of the product was 3.44 g (90%).

The product obtained was characterized by IR, Mass, $^{13}$C NMR and $^1$H NMR, which are as given below.

IR spectrum (cm$^{-1}$): 1375, 1398(O—SO$_2$ str.)

Mass spectrum (m/z): 214.1 (M+H)$^+$ $^{13}$C-NMR (DMSO-d$_6$): δ 170.3, 149.0, 139.5, 136.5, 121.9, 84.3, 81.2, 25.0, 14.0

$^1$H-NMR (DMSO-d$_6$): δ 7.44-8.46 (3H, m), 6.0 (1H, t), 4.69-5.10 (2H, m), 2.6 (2H, q), 2.1 (3H, s), 2.0 (3H, s), 1.1 (3H, t)

EXAMPLE 92

4-[2-(5-Ethyl-pyridin-2-yl)-2-hydroxy-ethoxy]-benzaldehyde (9a)

0.5 g (0.0023 mol) 5-ethyl-2-(2-oxo-[1,3,2]-dioxathiolan-4-yl)-pyridine was added into solution of 0.343 g (0.0027 mol) p-hydroxy benzaldehyde dissolved in 5 mL DMF. Reaction mixture was heated at 80° C. for 14 hr. Subsequent work up furnished 0.3 g (47%) the desired product.

The product obtained was characterized by IR, Mass, $^{13}$C NMR and $^1$H NMR, which was found to be identical with the product obtained in example 17. The impurity of regio isomer 4-[1-(5-ethyl-pyridin-2-yl)-2-hydroxy-ethoxy]-benzaldehyde as described in example 17 was also obtained 0.2 g (31%).

EXAMPLE 93

4-[2-Chloro-2-(5-ethyl-2-pyridyl)-ethoxy]-benzaldehyde (9, X═Cl)

To a stirred solution of 5 g (0.018 mol) 4-[2-(5-ethyl-pyridin-2-yl)-2-hydroxy-ethoxy]-benzaldehyde dissolved in chloroform was added 2.63 g (0.022 mol) thionyl chloride at 55-60° C. Reaction mixture was refluxed for 1 hr. Progress of the reaction was monitored by TLC and after completion of reaction, subsequent work-up in alkaline water yielded 4 g (75%) of the desired product.

The product obtained was characterized by Mass, $^{13}$C NMR and $^1$H NMR, which are as given below.

Mass spectrum (m/z): 290.1 (M+H)$^+$ $^{13}$C-NMR (DMSO-d$_6$): δ 190.5, 162.9, 153.5, 149.2, 139.3, 136.2, 131.4, 130.2, 122.4, 114.8, 71.0, 59.5, 25.6, 15.0

$^1$H-NMR (DMSO-d$_6$): δ 9.8 (1H, s), 6.91-8.45 (7H, m), 5.29 (1H, dd), 4.72 (1H, dd), 4.56 (1H, dd), 2.65 (2H, q), 1.24 (3H, t)

EXAMPLE 94

4-[2-Bromo-2-(5-ethyl-pyridin-2-yl)-ethoxy]-benzaldehyde (9, X═Br)

2.93 g (0.01 mol) PBr$_3$ was added to a solution of 5 g (0.018 mol) 4-[2-(5-ethyl-pyridn-2-yl)-2-hydroxy-ethoxy]-benzaldehyde dissolved in 50 mL chloroform at 55-60° C. Reaction mixture was refluxed for 1 hr. Progress of the reaction was monitored by TLC and after completion of reaction, subsequent work-up in alkaline water furnished 3 g (50%) of desired product.

EXAMPLE 95

5-{4-[2-Chloro-2-(5-ethyl-pyridin-2-yl)-ethoxy]-benzylidene}-2,4-thiazolidine dione (13, X═Cl)

A mixture of 2 g (0.017 mol) thiazolidin-2,4-dione, 2 g (0.034 mol) acetic acid and 3 g (0.03 mol) piperidine were added to a solution of 5 g (0.017 mol) 4-[2-chloro-2-(5-ethyl-pyridn-2-yl)-ethoxy]-benzaldehyde dissolved in 50 mL toluene. Reaction mixture was heated and water was removed azeotropically. After completion of the reaction on TLC, toluene was distilled out completely under reduced pressure. Product was poured into excess of water and extracted with ethyl acetate. After concentrating ethyl acetate in vacuo and making its HCl salt in usual way 4.3 g (60%) desired product obtained.

The product obtained was characterized by IR, Mass, $^{13}$C NMR and $^1$H NMR, which are as given in example 79.

EXAMPLE 96

5-{4-[2-Bromo-2-(5-ethyl-pyridin-2-yl)-ethoxy]-benzylidene}-2,4-thiazolidine dione (13, X═Br)

To stirred solution of 5 g (0.015 mol) 4-[2-bromo-2-(5-ethyl-pyridn-2-yl)-ethoxy]-benzaldehyde dissolved in 50 mL toluene was added 1.85 g (0.015 mol) thiazolidin-2,4-dione followed by addition of 2 g (0.03 mol) acetic acid and 3 g (0.03 mol) piperidine. Reaction mixture was heated and water was removed azeotropically. After completion of the reaction on TLC, toluene was distilled out completely under reduced pressure. Product was poured into excess of water and extracted with ethyl acetate. On concentrating ethyl acetate in vacuo, 0.65 g (10%) desired product obtained with satisfactory mass. The $^1$H NMR was similar to the $^1$H NMR of example 79.

EXAMPLE 97

4-[2-(5-Ethyl-pyridn-2-yl)-2-mesyl-ethoxy]-benzaldehyde (9, X═OMs)

0.89 g (0.0088 mol) triethyl amine was added to a solution of 0.2 g (0.0007 mol) 4-[2-(5-ethyl-pyridn-2-yl)-2-hydroxy-ethoxy]-benzaldehyde and 0.098 g (0.0008 mol) mesyl chloride dissolved in 5 mL dichloromethane at 0-5° C. Reaction mixture was stirred at 0-5° C. for 4 hr. Progress of the reaction was monitored by TLC and after completion of reaction, substantial work-up in excess water yielded 0.18 g (70%) of the desired product. The product obtained was characterized by Mass and $^1$H NMR, which are as given below.

Mass spectrum (m/z): 350.2 (M+H)$^+$ $^1$H-NMR (DMSO-d$_6$): δ 9.8 (1H, s), 7.15-8.48 (7H, m), 5.98 (1H, t), 4.58 (2H, d), 3.25 (3H, s), 2.65 (2H, q), 1.19 (3H, t)

EXAMPLE 98

5-{4-[2-(5-Ethyl-pyridin-2-yl)-2-mesyl-ethoxy]-benzylidene}-2,4-thiazolidine dione (13, X=OMs)

To a stirred solution of 0.65 g (0.0018 mol) 4-[2-(5-ethyl-pyridn-2-yl)-2-mesyl-ethoxy]-benzaldehyde dissolved in 10 mL toluene was added 0.211 g (0.0018 mol) thiazolidin-2,4-dione followed by addition of 0.161 g (0.03 mol) acetic acid and 0.228 g (0.03 mol) piperidine. Reaction mixture was refluxed at 120-130° C. for 4 hr. After completion of reaction on TLC, subsequent work-up gave the titled product. Yield of the product was 0.24 g (29%). The product obtained was identical to the product obtained in example 69.

EXAMPLE 99

4-[2-(5-Ethyl-pyridn-2-yl)-2-tosyl-ethoxy]-benzaldehyde (9, X=OTs)

0.44 g (0.0044 mol) triethyl amine was added to a solution of 1 g (0.0036 mol) 4-[2-(5-ethyl-pyridin-2-yl)-2-hydroxy-ethoxy]-benzaldehyde and 0.7 g (0.0036 mol) tosyl chloride dissolved in 25 mL dichloromethane at 0-5° C. Reaction mixture was stirred at 0-5° C. for 4 hr. Progress of the reaction was monitored by TLC and after completion of reaction, substantial work-up in excess water yielded the desired product. Yield of the product was 1 g (70%).

The product obtained was characterized by Mass and $^1$H NMR, which are as given below.

Mass spectrum (m/z): 426.2 (M+H)$^+$ $^1$H-NMR (DMSO-d$_6$): δ 9.87 (1H, s), 6.76-8.38 (11H, m), 5.84 (1H, dd), 4.37-4.49 (2H, dd), 2.66 (2H, q), 2.40 (3H, s), 1.26 (3H, t)

EXAMPLE 100

5-{4-[2-(5-Ethyl-pyridn-2-yl)-2-tosyl-ethoxy]-benzylidene}-2,4-thiazolidine dione (13, X=OTs)

To 1 g (0.0023 mol) 4-[2-(5-ethyl-pyridn-2-yl)-2-tosyl-ethoxy]-benzaldehyde dissolved in 15 mL toluene was added 0.27 g (0.0023 mol) thiazolidin-2,4-dione. To this 0.21 g (0.0035 mol) acetic acid and 0.3 g (0.0035 mol) piperidine were added. Reaction mixture was refluxed at 120-130° C. for 4 hr. After completion of reaction on TLC, substantial work-up gave the titled product. Yield of the product was 0.36 g (30%).

The product obtained was identical to the product obtained in example 74.

EXAMPLE 101

5-{4-[2-(5-Ethyl-pyridin-2-yl)-ethoxy]-benzyl}-2,4-thiazolidene dione (1)

In a mixture of 8 mL methanol and 2 mL (0.035 mol) acetic acid, 5 g (0.0115 mol) of 5-{4-[2-chloro-2-(5-ethyl-pyridn-2-yl)-ethoxy]-benzyl}-2,4-thiazolidine dione was dissolved and to this under stirring was added 0.3 g (0.0046 mol) zinc, at 25-30° C. and stirring was continued for 14 hours. Reaction mixture was poured in access water, made alkaline using 10% Na$_2$CO$_3$ and extracted with ethyl acetate. Ethyl acetate was dried (magnesium sulfate) and concentrated in vacuo. Methanol was added to the residual mass obtained which led to the formation of the desired product. Yield of the product was 2.05 g (45%). m.p. 173° C.

The product obtained was characterized by IR, Mass, $^{13}$C NMR, and $^1$H NMR, which was found to be identical with the product obtained in example 17.

Pharmaceutical compositions containing the novel compounds 13 and 14 or their salts, of the present invention may be prepared by conventional techniques as are well known in the art, e.g. as described in *Remington: the Science and Practice of Pharmacy*, 19$^{th}$ Ed., 1995. The compositions may be in the conventional forms, such as capsules, tablets, powders, solutions, suspensions, syrups, aerosols or topical applications. They may contain suitable solid or liquid carriers or in suitable sterile media to form injectable solutions or suspensions. The compositions may contain 0.5 to 20%, preferably 0.5 to 10% by weight of the active compound, the remaining being pharmaceutically acceptable carriers, excipients, diluents, solvents and the like as are well known.

The novel compounds 13 & 14 or their salts, in addition to being useful as intermediates for the preparation of thiazolidinediones of formula 1, are also useful for the treatment and/or prophylaxis of disease caused by metabolic disorders such as hyperlipidemia, insulin resistance, hyperglycemia, obesity and the likes.

The novel compounds 13 & 14 or their salts, of the invention may be administered to a mammal, especially, a human in need of such treatment, prevention, elimination, alleviation or amelioration of diseases mentioned above.

In another aspect of the present invention, method of treatment and/or prevention of the diseases mentioned above are provided using the novel compounds 13 & 14 or their salts, of the present invention.

The novel process to manufacture Pioglitazone described in the present invention has the following advantages:

1. Less no of steps (4-6), especially the route 2 to 9 to 13 to 1; or 2 to 9 to 13 to 14 to 1.
2. Describes several new and novel intermediates eg., 9, 13, 14, 3 and 6.
3. Involves operational simplicity, as most of the intermediates involved are solids.
4. Offers opportunity to make cationic and protic salts, which will offer further operational simplicity during manufacturing and purification.
5. Involves high yielding solution phase chemistry and mild reaction conditions.
6. Provides pure intermediates and final product, due to operational simplicity and cleanliness of the reaction.
7. The process avoids use of unpleasant smelling acrylate derivatives and various other drawbacks mentioned in prior art.
8. The synthetic route offers opportunity to integrate 2-3 steps into one, thereby further enhancing operational simplicity.
9. All the above factors contribute to the cost effectiveness of the process and consequent better opportunities for commercialization.

We claim:
1. A compound of formula 9 or its salt

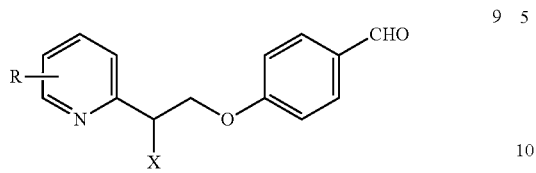

wherein R is a linear or branched $(C_1-C_6)$alkyl group; and X is selected from a member of the group consisting of Cl, Br, OMs, $OSO_3H$ and OTs.

2. The compound of claim 1 or its salt, wherein R is selected from the group consisting of butyl, iso-butyl, sec-butyl, tert-butyl, pentyl, iso-pentyl, neo-pentyl, and hexyl.

3. The compound of claim 1 or its salt, wherein R is selected from the group consisting of methyl, ethyl, propyl, and iso-propyl.

4. The compound of claim 1 or its salt, wherein R is 5-ethyl.

* * * * *